(12) United States Patent
Cole et al.

(10) Patent No.: US 7,531,363 B2
(45) Date of Patent: May 12, 2009

(54) PARTICLE DETECTION USING FLUORESCENCE

(75) Inventors: Barrett E. Cole, Bloomington, MN (US); Yuandong Gu, St. Paul, MN (US)

(73) Assignee: Honeywell International Inc., Morristown, NJ (US)

( * ) Notice: Subject to any disclaimer, the term of this patent is extended or adjusted under 35 U.S.C. 154(b) by 876 days.

(21) Appl. No.: 10/748,398

(22) Filed: Dec. 30, 2003

(65) Prior Publication Data

US 2005/0147533 A1    Jul. 7, 2005

(51) Int. Cl.
*G01N 21/64* (2006.01)

(52) U.S. Cl. .................. 436/172; 436/164; 422/73; 422/82.08; 73/28.04; 73/28.05

(58) Field of Classification Search .............. 422/3; 324/76.36; 73/28.05; 435/7.92; 250/458.1, 250/461.1; 436/86, 151, 172; 356/454, 326, 356/72; 359/198; 374/10; 378/45
See application file for complete search history.

(56) References Cited

U.S. PATENT DOCUMENTS

| | | | | |
|---|---|---|---|---|
| 4,147,515 | A | * | 4/1979 | Haas et al. ............ 436/151 |
| 4,614,961 | A | | 9/1986 | Khan et al. |
| H188 | H | * | 1/1987 | Thomson et al. |
| 4,651,010 | A | * | 3/1987 | Javan ................ 250/458.1 |
| 4,752,694 | A | | 6/1988 | Hegel, Jr. et al. |
| 4,754,139 | A | | 6/1988 | Ennulat et al. |
| 4,926,679 | A | * | 5/1990 | Dewhurst ............ 73/28.05 |
| 4,956,686 | A | | 9/1990 | Borrello et al. |
| 5,021,663 | A | | 6/1991 | Hornbeck |
| 5,076,097 | A | | 12/1991 | Zarrin et al. |
| 5,146,465 | A | | 9/1992 | Khan et al. |
| 5,278,435 | A | | 1/1994 | Van Hove |
| 5,286,976 | A | | 2/1994 | Cole |
| 5,293,041 | A | | 3/1994 | Kruse, Jr. |
| 5,300,777 | A | | 4/1994 | Goodwin |
| 5,300,915 | A | | 4/1994 | Higshi et al. |
| 5,520,881 | A | * | 5/1996 | Koestler et al. ............ 422/3 |
| 5,550,373 | A | | 8/1996 | Cole et al. |

(Continued)

FOREIGN PATENT DOCUMENTS

EP    0177918    4/1986

(Continued)

OTHER PUBLICATIONS

Agashe, et al., "Thermodynamics of the Complex Protein Unfolding Reaction of Barstar," Biochemistry, 36, pp. 12288-12295, 1997.

(Continued)

*Primary Examiner*—Walter D Griffin
*Assistant Examiner*—Christine T Mui
(74) *Attorney, Agent, or Firm*—Kris T. Fredrick

(57) ABSTRACT

Detection systems and methods for capturing and analyzing particles within a particle sample are provided. The detection system may include, for example, a particle concentrator that can be used to collect and concentrate particles on a sample collection surface, an energy source for providing energy to induce fluorescence in the particles, and a detector for detecting at least some fluorescence induced in the particles by the energy source. The detection system may include a heater and/or cooler for controlling the temperature of the particle sample during testing.

40 Claims, 20 Drawing Sheets

U.S. PATENT DOCUMENTS

| | | | |
|---|---|---|---|
| 5,674,698 A * | 10/1997 | Zarling et al. | 435/7.92 |
| 5,677,538 A | 10/1997 | Moustakas et al. | |
| 5,679,965 A | 10/1997 | Schetzina | |
| 5,701,012 A | 12/1997 | Ho | |
| 5,739,554 A | 4/1998 | Edmond et al. | |
| 5,771,094 A * | 6/1998 | Carter et al. | 356/326 |
| 5,834,331 A | 11/1998 | Razeghi | |
| 5,847,397 A | 12/1998 | Moustakas | |
| 5,900,650 A | 5/1999 | Nitta | |
| 5,909,280 A * | 6/1999 | Zavracky | 356/454 |
| 5,992,215 A * | 11/1999 | Caron et al. | 73/24.01 |
| 5,999,250 A | 12/1999 | Hairston et al. | |
| 6,080,988 A | 6/2000 | Ishizuya et al. | |
| 6,097,031 A | 8/2000 | Cole | |
| 6,230,572 B1 | 5/2001 | Pui et al. | |
| 6,238,085 B1 * | 5/2001 | Higashi et al. | 374/10 |
| 6,287,940 B1 | 9/2001 | Cole et al. | |
| 6,295,130 B1 | 9/2001 | Sun et al. | |
| 6,296,779 B1 | 10/2001 | Clark et al. | |
| 6,324,192 B1 | 11/2001 | Tayebati | |
| 6,388,789 B1 * | 5/2002 | Bernstein | 359/198 |
| 6,590,710 B2 | 7/2003 | Hara et al. | |
| 6,614,215 B1 * | 9/2003 | Wood | 324/76.36 |
| 6,762,056 B1 * | 7/2004 | Peeters | 436/86 |
| 7,057,712 B2 * | 6/2006 | Beck et al. | 356/72 |
| 2002/0018385 A1 | 2/2002 | Flanders et al. | |
| 2002/0031155 A1 | 3/2002 | Tayebati et al. | |
| 2003/0052281 A1 * | 3/2003 | Rader et al. | 250/461.1 |

FOREIGN PATENT DOCUMENTS

| | | |
|---|---|---|
| EP | 0475525 | 3/1992 |
| EP | 0481552 | 4/1992 |
| EP | 0654826 | 5/1995 |
| EP | 0667548 | 8/1995 |
| EP | 0687923 | 12/1995 |
| JP | 03252172 | 11/1991 |
| JP | 05095130 | 4/1993 |
| JP | 0728833 | 10/1995 |
| WO | 93/26049 | 12/1993 |
| WO | 97/18589 | 5/1997 |

OTHER PUBLICATIONS

Brown, J. et al., "Visible-Blind UV Digital Camera Based on a 32*32 Array of GAN/AlGAN P-I-N Photodiodes", MRS Internet Journal of Nitride Semiconductor Research, vol. 4S1, Sep. 1999, XP000949328 ISSN: 1092-5783.

Chitica, J., et al., "Monolithic InP-Based Tunable Filter with 10-nm Bandwidth for Optical Data Interconnects in the 1550-nm Band," IEEE Photonics Technology Letters, vol. 11, No. 5, pp. 584-586, May 1999.

Chung, S. W. et al., "Design and fabrication of 10×10 micro-spatial light modulator array for phase and amplitude modulation," Sensors and Actuators, vol. 78 No. 1, pp. 63-70, Jan. 1999.

Cole, et al., "Microscopic Spectroscopy of Optical MEMS Devices," Topic 2 (Materials and Technology), Honeywell Laboratories, 2 page abstract, submitted on or around Dec. 11, 2000.

Gorinstein et al., "Structure characterization of human serum proteins in solution and dry state," J. Peptide Res., 59, pp. 71-78, 2002.

http://particle.tsi.com/, TSI Particle Instruments, 2 pages, printed Dec. 10, 2003.

http://www.crti.drdc-rddc.gc.ca/projects/crti_0011ta_e.html, CRTI 0011TA—Hand-Held Real Time Biological Agent Detector—CBRN Research . . . , 2 pages, printed Dec. 10, 2003.

http://www.opticsreport.com/content/interview.php?interview_id=3020, Optics Report, 5 pages, printed Dec. 10, 2003.

http://www.suffield.drdc-rddc.gc.ca/ResearchTech/Products/CB_PRODUCTS/RD98002, CIBADS, 5 pages, printed Dec. 10, 2003.

http://www.suffield.drdc-rddc.gc.ca/ResearchTech/Products/CB_PRODUCTS/RD98001, FLAPS, 4 pages, printed Dec. 10, 2003.

http://www.tsi.com/exposure/products/dusttrak/dusttrak.htm, DUSTTRAK Aerosol Monitor Model 8520, 4 pages, printed Dec. 10, 2003.

Jerman, J.H., et al., "A miniature Fabry-Perot interferometer with a corrugated silicon diaphragm support," Sensors and Actuators, vol. !29, No. 2, pp. 151-158, Nov. 1991.

Johnson-Winegar, Dr. Anna, "Fighting Bioterrorism: Using America's Scientists and Entrepreneurs to Find Solutions," Statement of Dr. Anna Johnson-Winegar, before the Senate Committee on Commerce, Science, and Subcommittee on Science, Technology, and Space, 10 pages, Feb. 5, 2002.

Molnar, R.J., "Materials/Substrate Issues for UV Light Emitters," MIT Lincoln Laboratory, 22 pages, Apr. 9, 2001.

Muller, J., et al., "Thermal Denaturing of Bacteriorhodopsin by X-Ray Scattering from Oriented Purple Membranes," Biophysical Journal, vol. 78, pp. 3208-3217, Jun. 2000.

Nolting, "Temperature-Jump Induced Fast Refolding of Cold-Unfolded Protein," Biochemical and Biophysical Research Communications 227, pp. 903-908, 1996.

Sze. "Physics of Semiconductor Devices." pp. 763-765, John Wiley & Sons, N.Y., 1982.

Tayebati, P., et al., "Microelectromechanical tunable filter with stable half symmetric cavity," Electronics Letters, IEE Stevanage, GB, vol. 34, No. 20, pp. 1967-1968, Oct. 1998.

Tayebati, P., et. al., "Widely Tunable Fabry-Perot Filters using High Index-contrast DBRs," Design and Manufacturing of WDM Devices, Dallas, Texas, Nov. 4-5, 1997, SPIE vol. 3234, pp. 206-218, 1998.

U.S. Appl. No. 09/275,632, filed Mar. 24, 1999, entitled "Back Illuminated Heterojunction Photodiode."

U.S. Appl. No. 10/100,298, filed Mar. 18, 2002, entitled "Spectrally Tunable Detector."

Yang W. et al., "Back-Illuminated GAN/AlGAN Heterojunction Photodiodes With High Quantum Efficiency and Low Noise," Applied Physics Letters, vol. 73, No. 8, Aug. 24, 1998, pp. 1086-1088, XP000777678.

* cited by examiner

PARTICLE DETECTION USING FLUORESCENCE

This invention was made with government support under contract number N00014-00-C-0407. The government may have certain rights in the invention.

TECHNICAL FIELD

The present invention generally relates to systems and methods for detecting particles in a sample, and more particularly, to systems and methods for detecting bio-particles.

BACKGROUND

Aerosols composed of biological particles include a small fraction of the aerosols present in our atmosphere. Nonetheless, there is an increasing interest in analyzing biological aerosols, which can incorporate bacteria, fungi, pollens and other biological particles. Certain diseases, for example, tuberculosis, influenza and pneumonia, are transmitted via airborne particles or droplets. Diseases that affect livestock and other farm animals, (e.g. anthrax and brucellosis) and diseases that affect crops, likewise are transmitted through the air. In addition, airborne pollens can cause allergic reactions in humans.

The recent rise in terrorist activities and potential military confrontations with rogue nations has increased concerns over the viability of weapons of mass destruction such as biological weapons. Biological weapons can include biological agents such as *bacillus anthracis* (anthrax), cholera toxin, influenza, and smallpox virus, among others. Military personnel in the field can be exposed to biological agents in a variety of ways, such as by exploding a device in the vicinity of the target, by releasing one or more agents at a location upwind from the target area, etc. In addition, biological agents may be delivered to occupants within a civilian or military building by releasing the agents within the building or external to the building but close to an air intake of the building. The building's heating, ventilating, and air conditioning (HVAC) system may then rapidly deliver the released biological agent into and/or throughout the building.

As such, the study of airborne bioparticles is now recognized as a key concern, and has an increased role in such diverse areas as epidemiology, DNA genomic analysis and other medical fields, agriculture, building management, food- and water-quality monitoring, and defense, to name just a few. A number of systems have been developed to detect bioparticles in a sample. However, most of these systems are large and expensive, and are not amenable to large scale production and use.

SUMMARY

The present invention provides methods and system for detecting bioparticles in a sample. The systems of the present invention may be smaller and less expensive that other systems that are currently available, and may provide increased discrimination and sensitivity, as well as other advantages.

Biological cells typically contain fluorescent molecules, e.g. flavins, amino acids and nicotinamide adenine nucleotides, etc., and thus emit fluorescent signals when exposed to excitation energy within a range of excitation frequencies. The particular wavelengths found in the induced fluorescence may provide information to help reveal the identity and/or class of particles that are present in the particle sample. Thus, and in accordance with one illustrative embodiment of the present invention, a particle analyzer may be provided that includes a particle concentrator adapted to collect and concentrate particles and provide a particle sample to a sample collection surface. An energy source may be provided to induce fluorescence in the particles held by the sample collection surface, and a detector may be used to detect the induced fluorescence. Selected particles in the particle sample may be identified and/or classified by analyzing the induced fluorescence.

In some embodiments, the particle concentrator may be adapted to provide mass sorted particles to the sample collection surface, which may help provide a first level of particle discrimination based on mass. Also, it is contemplated that the detector may be adapted to detect various wavelengths of induced fluorescence, either simultaneously, sequentially, or some combination of both. In some cases, the detector may include a number of detector pixels, wherein each pixel is sensitive to one, two, or more wavelengths. Also, it is contemplated that adjustable filters may be provided in front of some or all of the detectors to adjust the sensitive wavelength of the detectors over time, providing additional flexibility. In some cases, one or more lenses may be used to help image at least some of the sample collection surface on multiple detectors. In this embodiment, each detector may be focused on one region of the sample collection surface.

In some embodiments, a heater and/or cooler may be thermally coupled to the sample collection surface to control the temperature of the sample. This may allow the use of temperature to provide additional discrimination and sensitivity, when desired. By controlling the temperature of the sample, a wavelength shift of the fluorescence spectrum can be induced and observed in, for example, a protein. Applying heat to a sample may, for example, cause a change in protein configuration, a dissociation of protein clusters, a protein unfolding, or even a protein denaturation. With the addition of heat, a protein can be transformed from a more compact state to a less folded state, exposing the buried hydrophobic surfaces, which sometimes results in a higher degree of solvent exposure of the aromatic side chains. In some cases, a change in florescence intensity can be observed along with, or separate from, a wavelength shift in the fluorescence spectrum.

In some embodiments, the humidity of the sample collection surface may also be controlled. The denaturation temperature of proteins can be extremely predictable in aqueous solution, which may also be used as an indicator for particle detection. When the sample is in a dry state, however, the denaturation temperature can be highly sensitive to humidity. Thus, in some embodiments, the humidity in or around the sample can be controlled. A constant humidity can be achieved by, for example, placing a saturated salt solution in the same enclosed chamber as the sample collecting surface but with little heat transfer between the two. This saturated salt solution may be, for example, sodium nitrate, sodium chloride, or any other compounds (may be mixture of several) that may offer different water partial pressures. In this configuration, a relatively constant humidity can be maintained in or around the sample. While this is one example, it is contemplated that the humidity in the sample collection chamber may be controlled by any suitable mechanism, as desired.

Some biological particles may emit more induced fluorescence and/or experience a particular spectrum shift at lower temperatures, and other biological particles may emit more induced fluorescence and/or experience a spectrum shift at higher temperatures than at lower temperatures. Thus, and in some embodiments, a heater and/or cooler may be provided to heat and/or cool the sample, preferably in accordance with a temperature profile. At selected temperatures along the temperature profile, the intensity and/or spectra of the induced fluorescence may be monitored to help reveal the identity and/or class of particles that are present in the particle sample. While the humidity is preferably maintained at a constant level, it is contemplated that the humidity may be controlled or varied to provide additional discrimination, if desired. In addition, it is contemplated that the pH level of the sample collection surface may be controlled, which in some cases, may also help provide additional discrimination, if desired. It is also contemplated that certain chemicals may be selectively added to the sample, which may help denature proteins to provide additional discrimination, if desired.

Once a sample is sufficiently analyzed, it is contemplated that the sample collection surface may be heated to a sufficient temperature to kill or burn off the particles on the sample collection surface in preparation for a new sample. To help reduce the energy required to heat and/or cool the sample collection surface, it is contemplated that the sample collection surface may be relatively thermally isolated from its surroundings.

The above summary of the present invention is not intended to describe each disclosed embodiment or every implementation of the present invention. The Figures, Detailed Description and Examples which follow more particularly exemplify these embodiments.

BRIEF DESCRIPTION OF THE FIGURES

The invention may be more completely understood in consideration of the following detailed description of various embodiments of the invention in connection with the accompanying drawings, in which.

Figure 1:
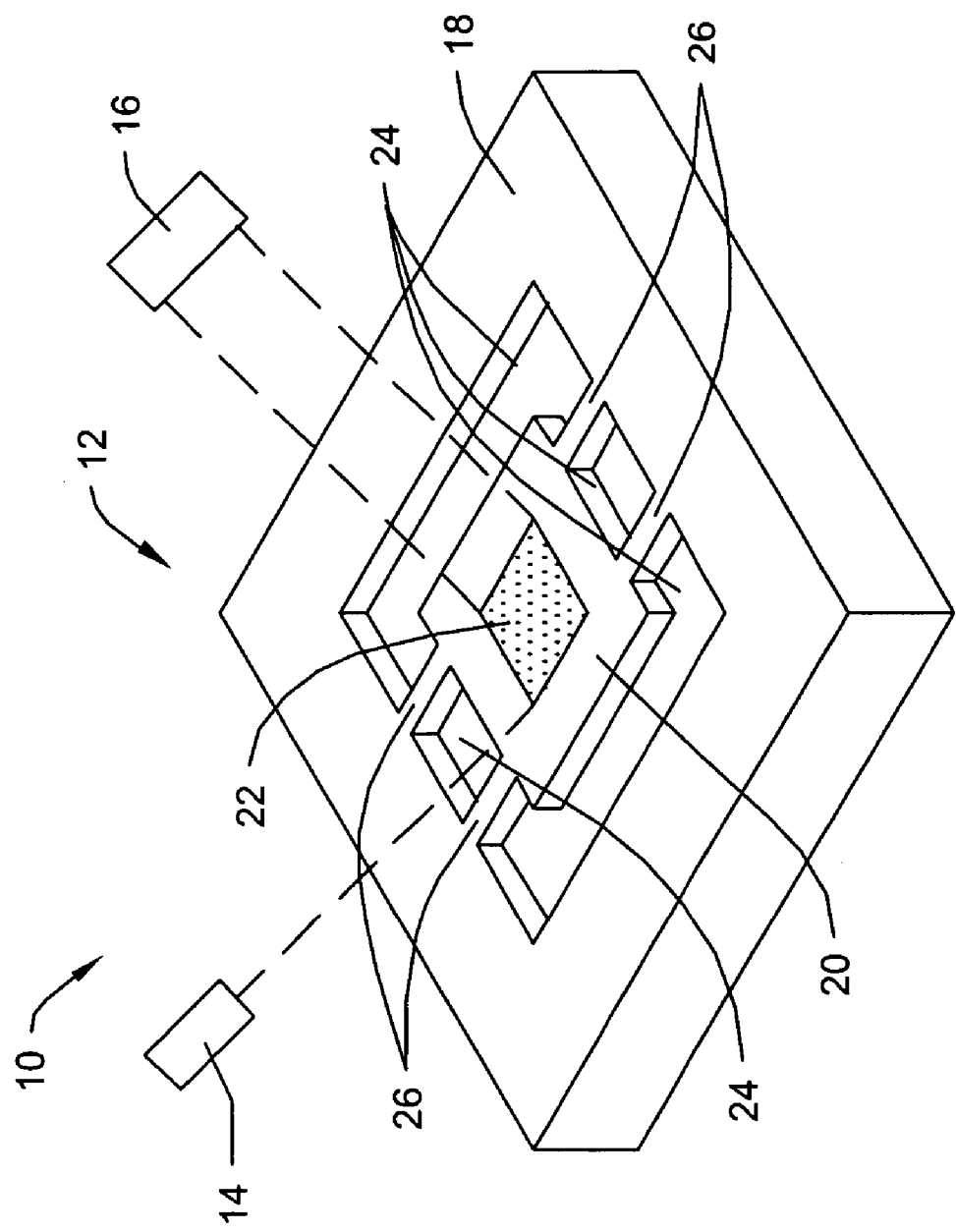
FIG. 1 is a schematic illustration of a detection system in accordance with an embodiment of the present invention.

While the invention is amenable to various modifications and alternative forms, specifics thereof have been shown by way of example in the drawings and will be described in detail. It should be understood, however, that the intention is not to limit the invention to the particular embodiments described. On the contrary, the intention is to cover all modifications, equivalents, and alternatives falling within the spirit and scope of the invention.

DETAILED DESCRIPTION

The following description should be read with reference to the drawings, in which like elements in different drawings are numbered in like fashion. The drawings, which are not necessarily to scale, depict selected embodiments and are not intended to limit the scope of the invention. Although examples of construction, dimensions, and materials are illustrated for the various elements, those skilled in the art will recognize that many of the examples provided have suitable alternatives that may be utilized.

Particular embodiments of the present invention are directed to detecting particles that emit induced fluorescence when exited by an energy source. This may include both chemical and/or biological particles. In some embodiments, the particles can include molecular scale particles such as chemical and/or biological agents. Biological agents can include such things as proteins, protein fragments and prions. Other examples of bioparticles can include bacteria and viruses.

Turning now to FIG. 1, an embodiment of a particle detection system 10 is illustrated. Detection system 10 includes a sampling platform 12, an energy source 14, and a detector 16. Sampling platform 12 includes a substrate 18, a support member 20 that can be integrally or separately formed with the substrate 18, and a sample collection surface 22 formed or placed atop support member 20.

Substrate 18 can be formed from any suitable material. In some embodiments, substrate 18 can be formed from a silicon wafer as will be described in greater detail below with respect to FIGS. 6-8. In other embodiments, substrate 18 can be formed from a glass material such as Pyrex® as illustrated for example in FIGS. 9-16. While silicon and glass are used for illustrative purposes, it is contemplated that any suitable substrate may be used, as desired.

Figure 2:
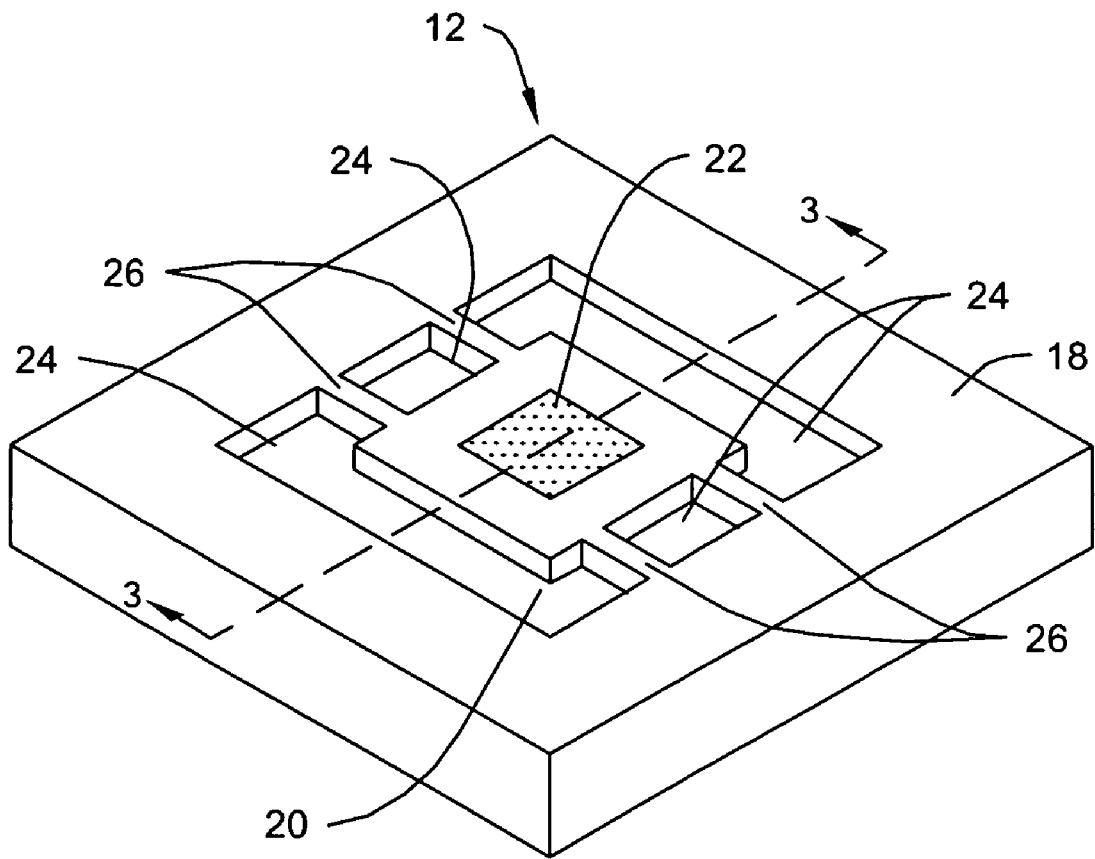
FIG. 2 is a schematic illustration of a sampling platform in accordance with an embodiment of the present invention.
Figure 3:
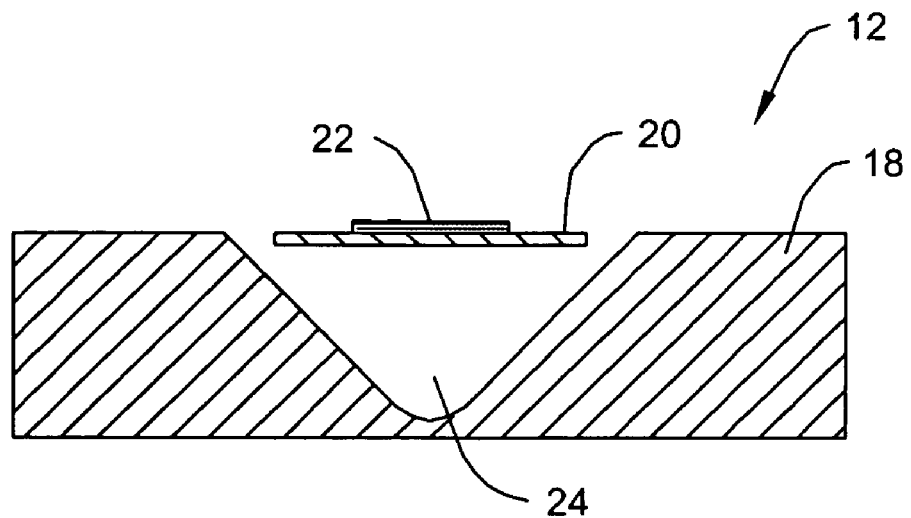
FIG. 3 is a cross-sectional view of the sampling platform of FIG. 2.

In some embodiments, support member 20 can be integrally formed with substrate 18. In other embodiments, support member 20 can be formed separately and then subsequently secured to substrate 18. In FIG. 1, support member 20 is at least partially thermally isolated from substrate 18. Substrate 18 includes a cavity 24 formed underneath and partially around support member 20. To assist in thermally isolating support member 20, support member 18 can include one or more legs 26 that connect or are integrally formed at one end with support member 20 and that connect or are integrally formed at a second end with substrate 18. FIGS. 2 and 3 illustrate sample platform 12. In particular, FIG. 3, which is a cross-section of FIG. 2, shows cavity 24 extending underneath support member 20 to help thermally isolate support member 20 from substrate 18.

Sample collection surface 22 can be formed of any suitable material that inherently or can be processed to provide desired characteristics. Sample collection surface 22 can be formed, for example, on the surface of support member 20. In some embodiments, sample collection surface 22 can be independently formed and subsequently secured to support member 20. A sample can be placed onto sample collection surface 22 using any suitable method. In some embodiments, the sample can be sprayed, dropped or wiped onto sample collection surface 22, as desired.

Desirable characteristics for sample collection surface include being sufficiently thermally resistant to any temperatures that sample collection surface 22 may be subjected to during use of detection system 10. In some embodiments, sample collection surface 22 can be formed of a material that provides a significant amount of surface area with respect to the overall dimensions of sample collection surface 22, as such a material can improve the particle retention characteristics of sample collection surface 22. Also, sample collection surface 22 can be formed of a material that exhibits a well-known and well-defined fluorescence when excited by energy at a given wavelength, and/or sample collection surface 22 can be formed of a material that exhibits no or substantially no fluorescence. In some embodiments, sample collection surface 22 can be formed of a high temperature adsorbate such as carbon nanotubes, and/or can be made sticky to help secure the sample particles to the sample collection surface 22.

The energy source 14 is preferably a laser, such as an Ultra Violet (UV) NDYAG laser. However, it is contemplated that the energy source 14 may be any suitable energy source that can deliver a desired wavelength or range of wavelengths at sufficient power levels. Vertical Cavity Surface Emitting Lasers (VCSELs), Light Emitting Diodes (LEDs) and other such device may be used in some embodiments.

The detector 16 can be any suitable detector that is adapted to detect light that is within a desirable wavelength range, and more particularly, a wavelength range that includes at least some of the expected induced fluorescence from particles with the particle sample. In some embodiments, detector 16 can be a visible light detector, an ultraviolet light, or any other suitable detector, as desired. In some embodiments, detector 16 can detect two or more wavelength bands, such as both visible and ultraviolet light.

In some embodiments, detector 16 can include one or more detector pixels, and each pixel can be adapted to read a single band of wavelengths or a plurality of wavelengths, as desired. For example, in some embodiments, detector 16 can include a plurality of pixels arranged in a first linear array each adapted to detect ultraviolet light. Detector 16 may also include a plurality of pixels arranged in a second linear array each adapted to detect visible light. In come embodiments, the first linear array and the second linear array can be positioned adjacent one another to provide detector 16 with the ability to detect both ultraviolet and visible light simultaneously. In some embodiments, at least some of the ultraviolet-sensitive pixels can be paired with at least some of the visible-light sensitive pixels.

Also, it is contemplated that the detector may be adapted to detect various wavelengths of induced fluorescence, either simultaneously, sequentially, or some combination of both. For example, an adjustable Fabry-Perot cavity may be provided in front of each detector, which can be used to adjust the sensitive wavelength of the detectors over a range of wavelengths over time. Some illustrative detectors that may be suitable are described in co-pending U.S. patent application Ser. No. 10/081,369, entitled "Dual Wavelength Spectrometer", which is incorporated herein by reference.

Figure 4:
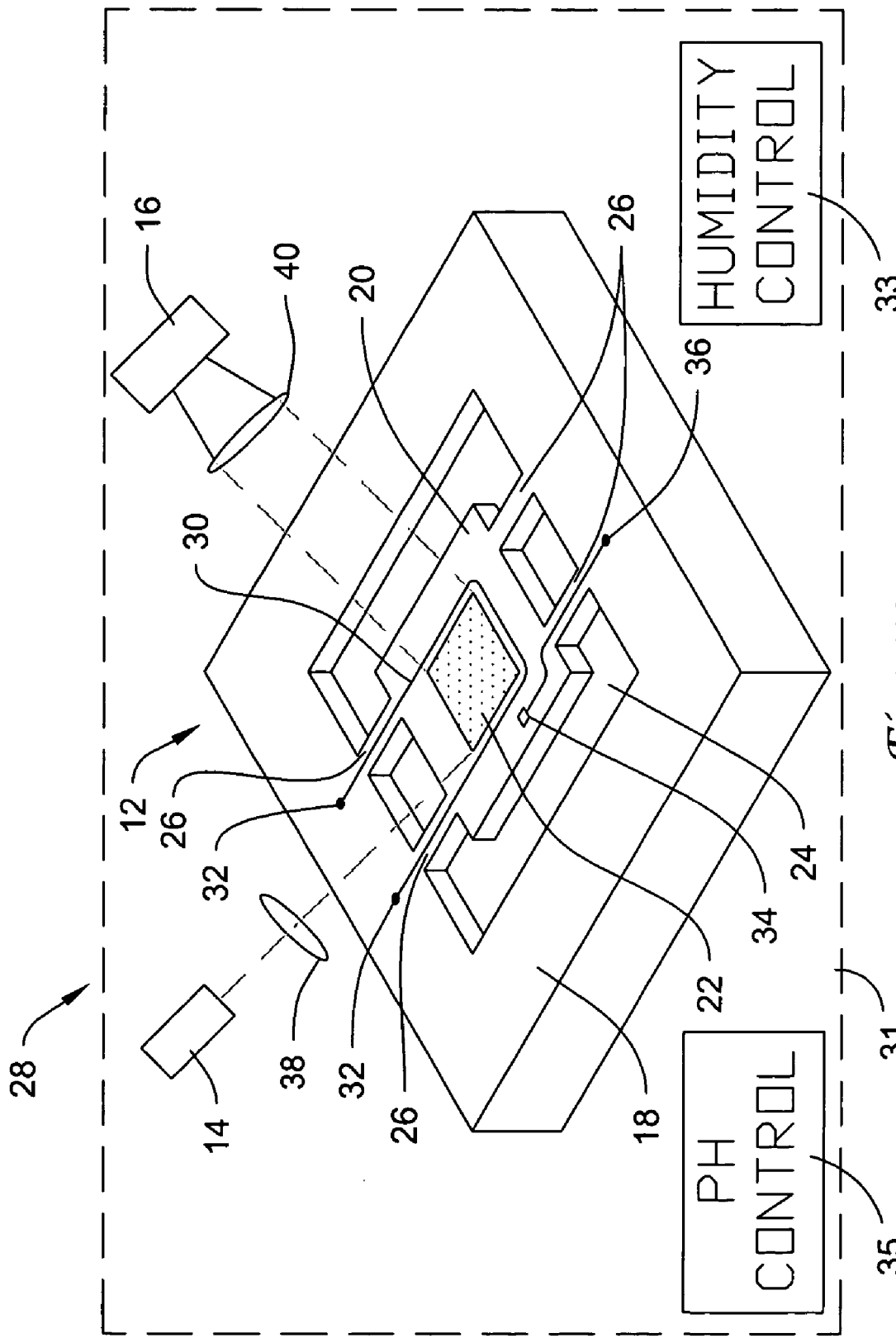
FIG. 4 is a schematic illustration of a detection system in accordance with an embodiment of the present invention.

Turning now to FIG. 4, another particle detection system 28 is illustrated. Detection system 28 includes sampling platform 12, energy source 14, and detector 16. In some embodiments, as illustrated, sampling platform 12 can include a thermoelectric device 30. Thermoelectric device 30 can be a heating element such as a resistive heating element and/or a thermoelectric cooling device. In either event, thermoelectric device 30 can terminate in electrical contacts 32 that can be used to power thermoelectric device 30.

Detection system 28 also includes a temperature sensor 34 that can be used in some embodiments to monitor the temperature of support member 20. Any suitable temperature sensor may be used. Temperature sensor 34 can terminate in an electrical contact 36, which can be used to provide communication between temperature sensor 34 and a controller (not shown), which will be discussed in greater detail hereinafter.

In some embodiments, as illustrated, detection system 28 can include an energy source lens 38 that can be adapted to focus energy from energy source 14 and direct it towards part or all of sample collection surface 22. Detection system 28 can also include a detector lens 40, which can be adapted to focus or image induced fluorescence onto a portion or all of detector 16. Lenses 38 and 40 can be selected from any suitable lenses having the desired characteristics. In some embodiments, as illustrated for example in FIG. 1, lenses 38 and 40 can be omitted, if desired.

In some embodiments, the humidity around the sample collection surface 22 may also be controlled by a humidity controller 33. As noted above, when the sample is in a dry state, the denaturation temperature of proteins can be highly sensitive to humidity. Thus, in some embodiments, the sample collection surface 22 can be provided in a sample collection chamber 31, and the humidity around the sample can be controlled by humidity controller 33. In one embodiment, the humidity controller 33 can include a saturated salt solution placed in the sample collection chamber 31. Preferably, the saturated salt solution is thermally isolated from the sample collection surface 22. The saturated salt solution may be, for example, sodium nitrate, sodium chloride, or any other compounds (may be mixture of several) that may offer different water partial pressures. In this configuration, the humidity controller 33 can provide a relatively constant humidity around the sample.

While the humidity controller 33 can include a salt solution or other compound to help control the humidity, it is contemplated that the humidity controller 33 may provide humidity control in any suitable way, as desired. In addition, and while the humidity controller 33 preferably maintains a relatively constant humidity level in the sample collection chamber 31, it is contemplated that the humidity controller 33 may vary the humidity in the sample collection chamber 31, sometimes in accordance with a humidity profile, which in some cases, may provide additional discrimination, if desired. In addition, it is contemplated that a PH controller 35 may be provided to help control and sometimes vary the PH level at the sample collection surface, which in some cases, may also help provide discrimination, if desired. In yet another embodiment, certain chemicals may be selectively added to the sample, which may help denature proteins to provide additional discrimination, if desired.

Figure 5:
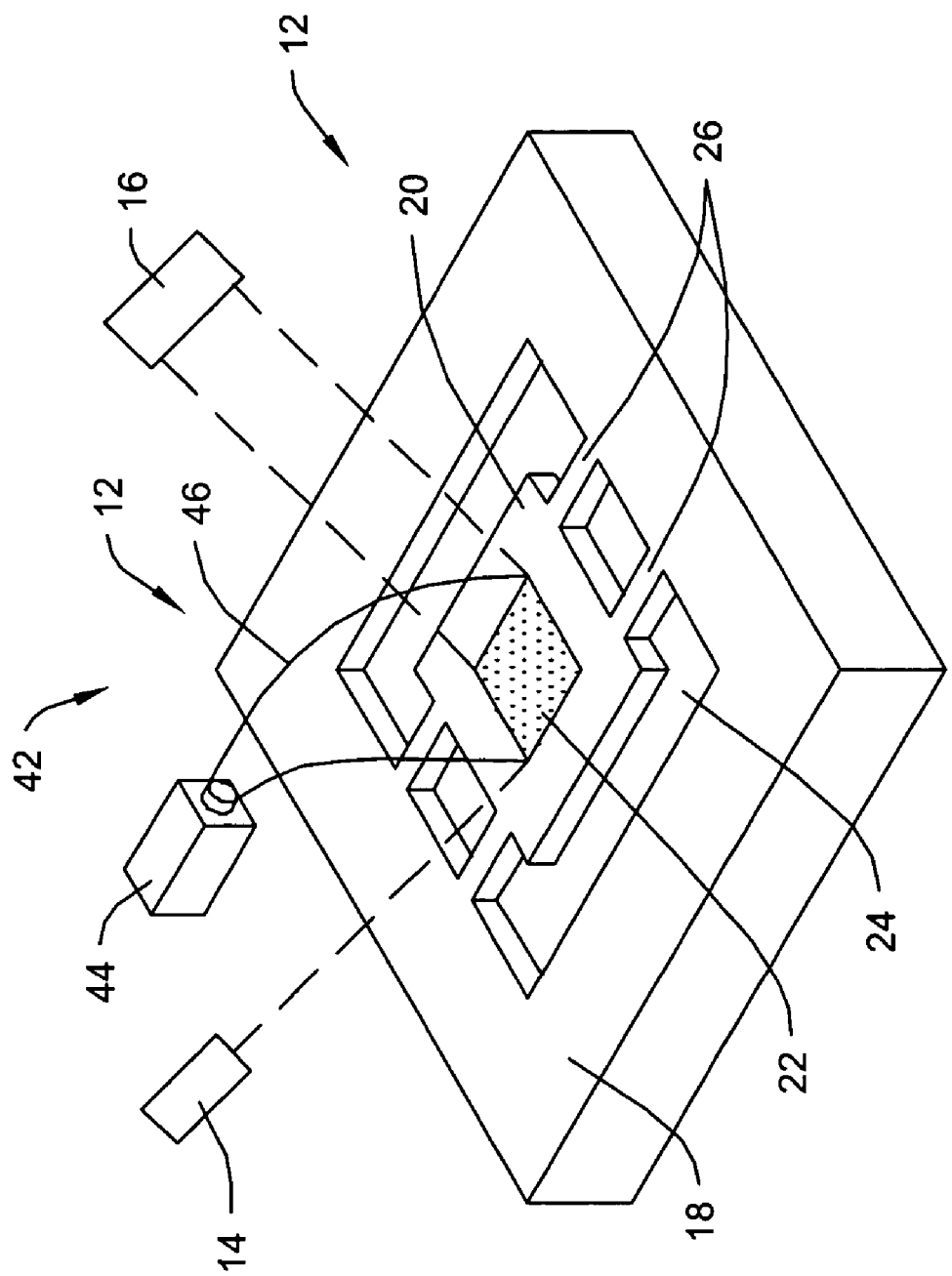
FIG. 5 is a schematic illustration of a detection system in accordance with an embodiment of the present invention.

FIG. 5 illustrates another detection system 42 that includes, as previously discussed, sampling platform 12, energy source 14, and detector 16. In some embodiments, as illustrated, detection system 42 can include a sample collector 44. Sample collector 44 can be adapted to collect particles such as bioparticles from aerosols and other suspended particles. In some embodiments, sample collector 44 can be adapted to concentrate the particles collected and can provide the concentrated particles to sample collection surface 22.

Sample collector 44 can also be adapted to throw the concentrated particles through a curved path 46 to reach sample collection surface 22. As a result, sample collector 44 can in some embodiments provide at least a rudimentary mass sorting of the concentrated particles, as heavier particles will tend to curve less while passing through curved path 46. One illustrative sample collector 44 is the MICROVIC™ Particle Concentrator, commercially available from Mesosystems of Albuquerque, N. Mex.

Figure 6:
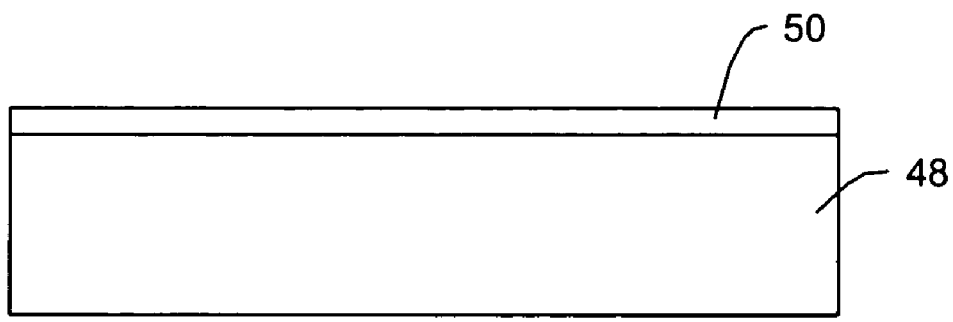
FIGS. 6-8 are schematic illustrations showing a step-by-step process of forming the sampling platform of FIG. 4.
Figure 7:
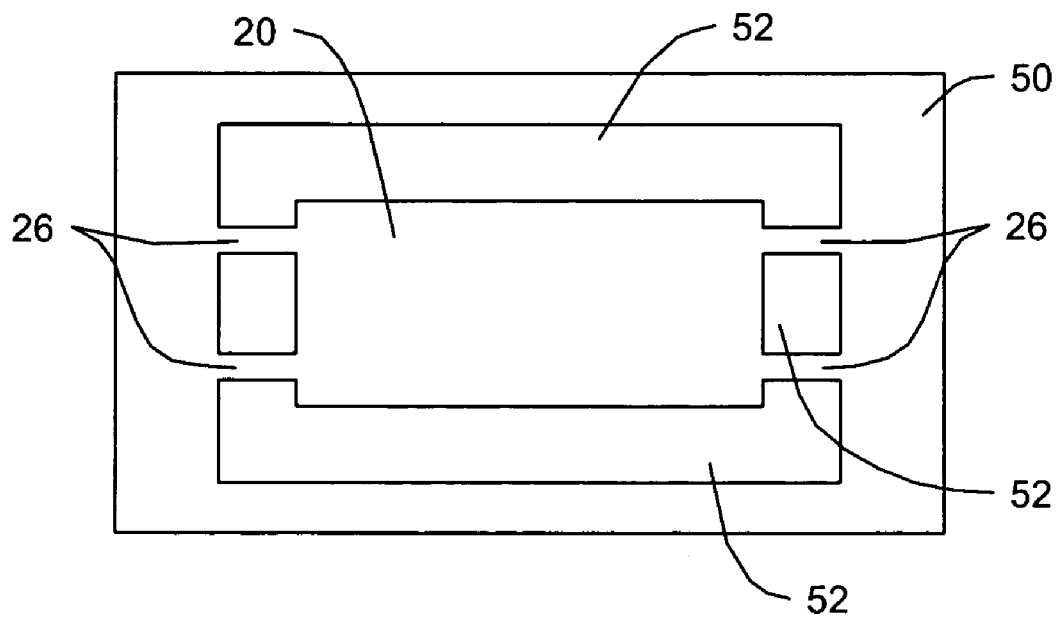
Figure 8:
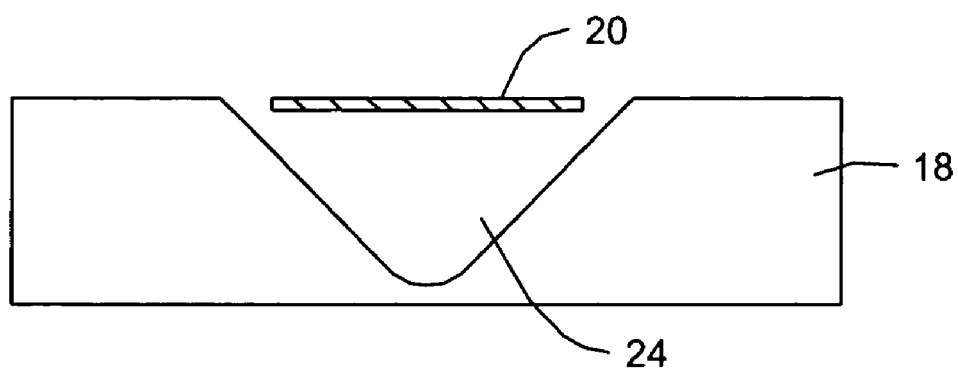

Sampling platform 12 can be manufactured using a variety of different methods. FIGS. 6-8 illustrate one illustrative method that employs a silicon wafer, and FIGS. 9-16 illustrate another illustrative method that employs a glass substrate. While silicon and glass are used for illustrative purposes, it is contemplated that any suitable substrate may be used, as desired.

FIG. 6 is a cross-sectional side view of a silicon wafer 48 with a mask layer 50 applied to one surface thereof. FIG. 7 is a top view of mask layer 50 after the mask layer has been patterned, preferably using photolithography. The patterned mask layer 50 is shown defining a ring around support member 20, with narrow legs 26 extending therefrom. With the mask layer 50 patterned, an etchant is introduced to etch away the exposed portions 52 of the substrate 48. As illustrated in FIG. 8, an anisotropic etch may be used to provide a cavity 24 below support member 20.

Figure 9:
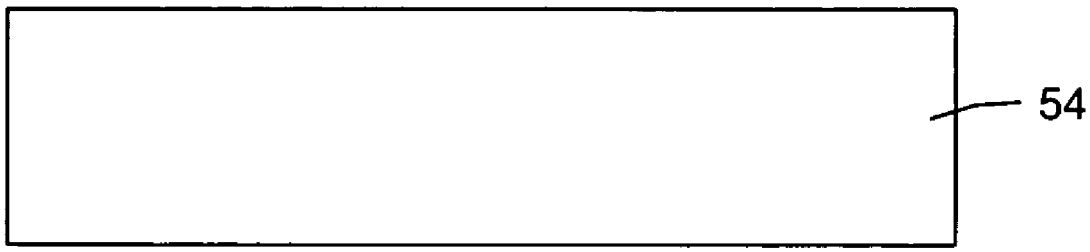
FIGS. 9-16 are schematic illustrations showing another step-by-step process of forming the sampling platform of FIG. 4.
Figure 10:
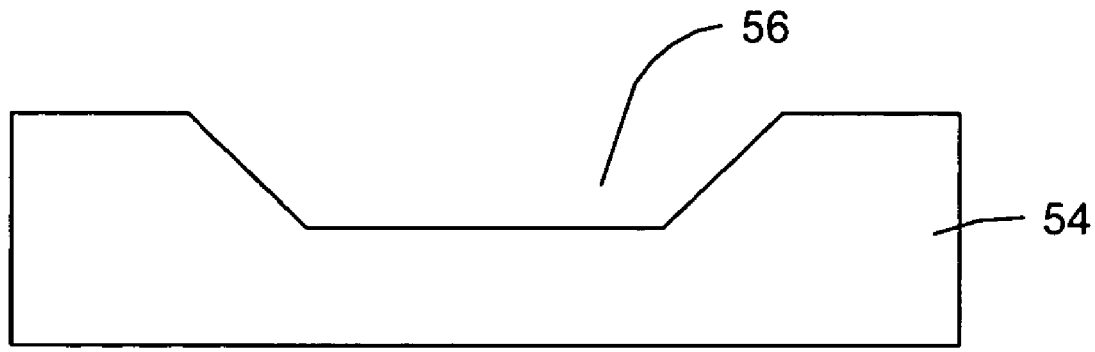
Figure 11:
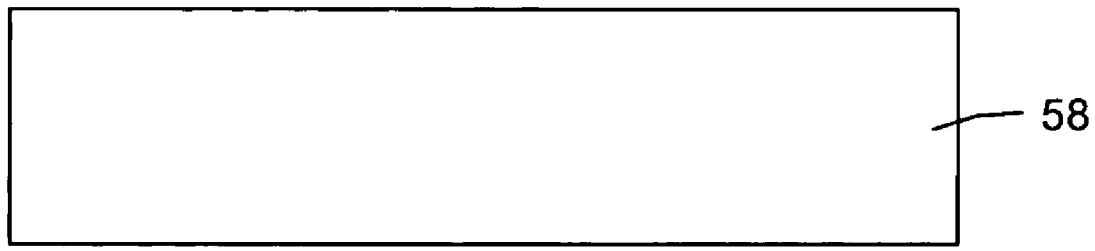
Figure 12:
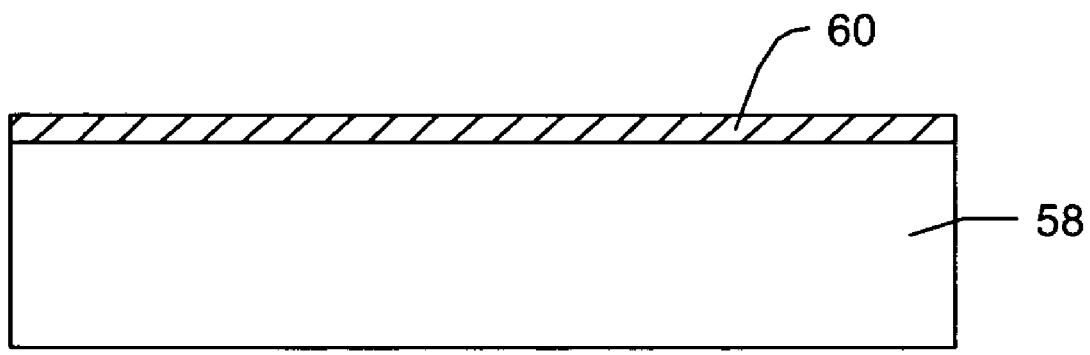

FIGS. 9-16 illustrate another method of forming sampling platform 12. FIG. 9 shows a glass substrate 54 that in some embodiments can be formed from PYREX®. In FIG. 10, glass substrate 54 has been etched or otherwise processed to form a depression 56 that will ultimately provide a cavity below a sampling platform 12. FIG. 11 shows a silicon wafer 58, and FIG. 12 shows the silicon wafer 58 with a boron doped epitaxial layer 60 grown thereon. While a boron doped epitaxial layer 60 is shown, it is contemplated that any suitable material may be used, including material or materials that can provide an etch stop when removing the bulk of the wafer, as further described below.

Figure 13:
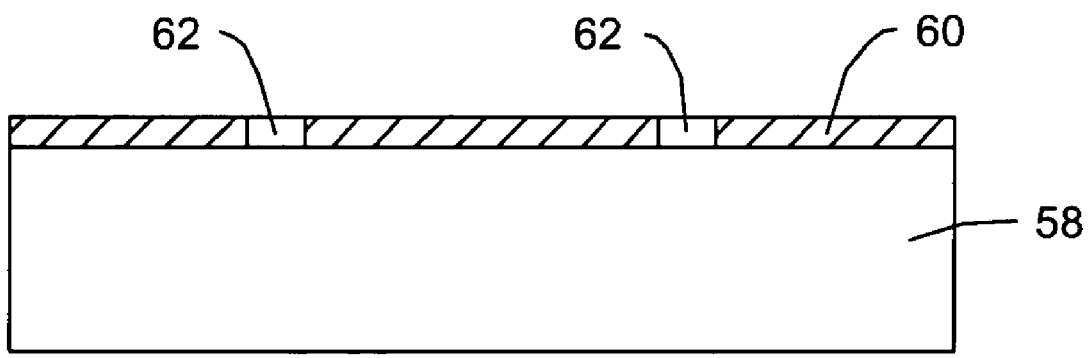
Figure 14:
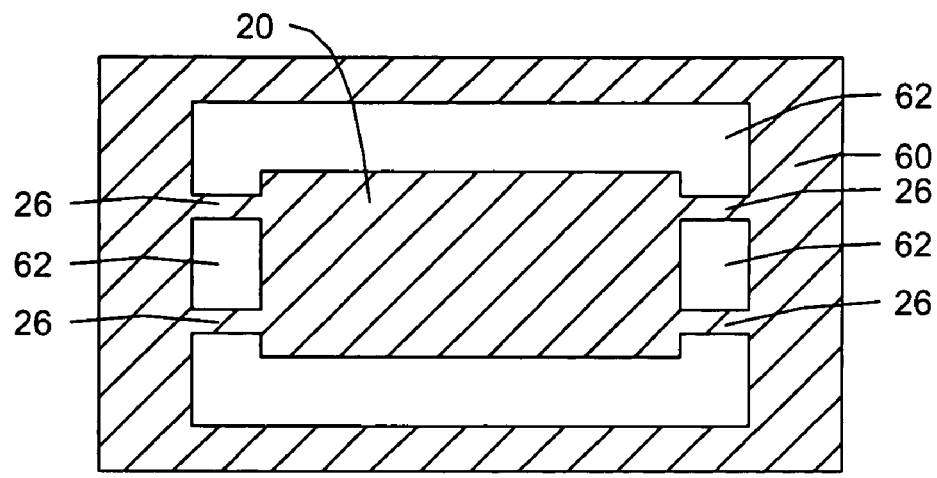

FIG. 13 shows that the boron doped epitaxial layer 60 after it has been patterned using, for example, a Deep Reactive Ion Etching (DRIE). The boron doped epitaxial layer 60 may be patterned to defining a ring around support member 20, with narrow legs 26 extending therefrom, as shown in FIG. 14.

Figure 15:
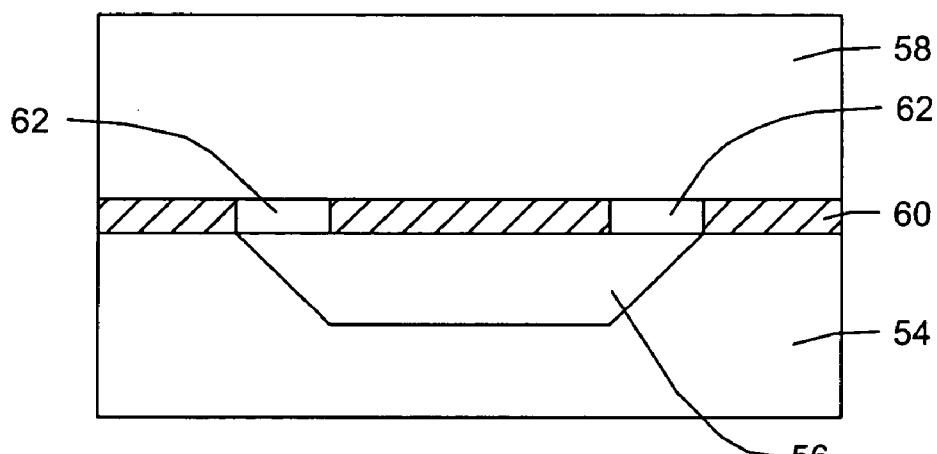
Figure 16:
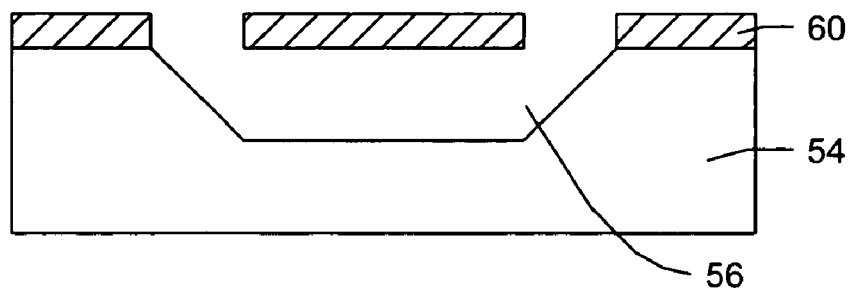

Next, the silicon wafer 58 bearing the patterned boron doped epitaxial layer 60 is inverted and placed onto glass block 54, as shown in FIG. 15. Silicon wafer 58 can be adhered to glass block 54 using, for example, anodic bonding, adhesives, or any other suitable method. Once the assembly has been secured together, the back side of the silicon wafer 58 is removed, as seen in FIG. 16. The patterned boron doped epitaxial layer 60 remains, forming support member 20 over cavity 56.

Figure 17:
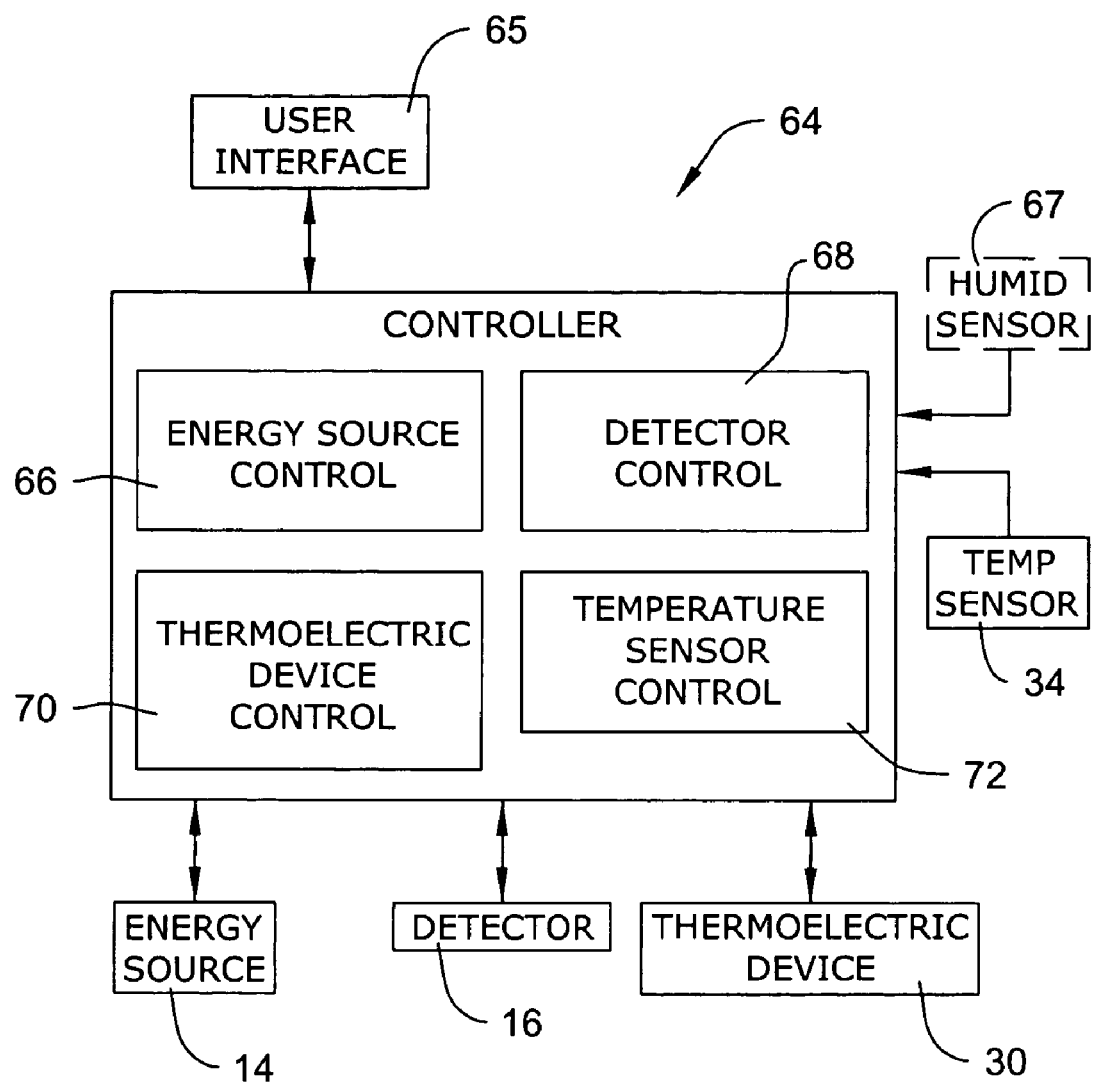
FIG. 17 is a schematic illustration of a controller in accordance with an embodiment of the present invention.
Figure 18:
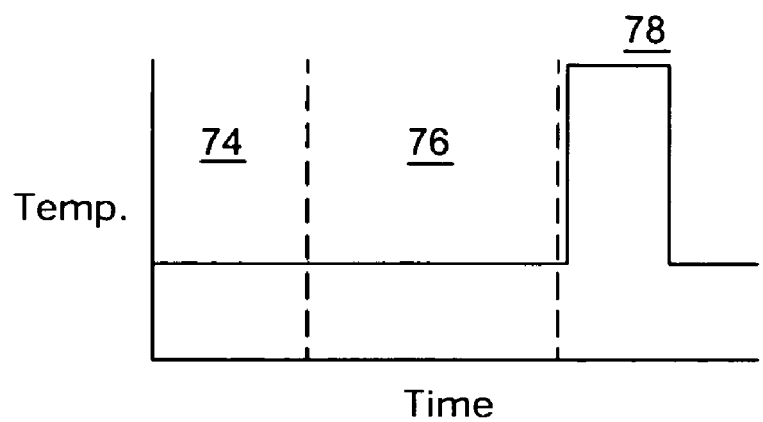
FIGS. 18-22 are schematic illustrations of suitable temperature profiles in accordance with an embodiment of the present invention.
Figure 19:
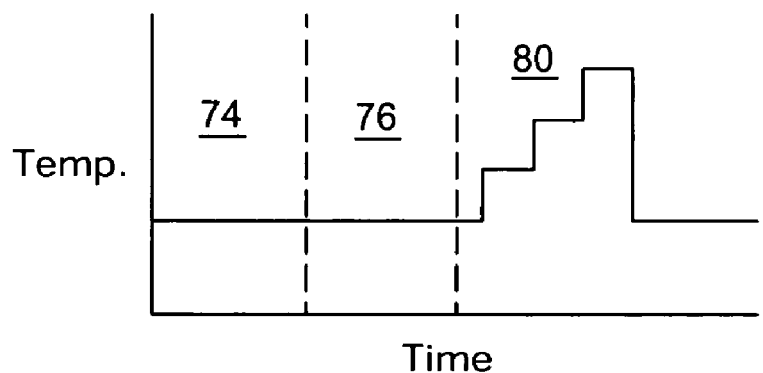
Figure 20:
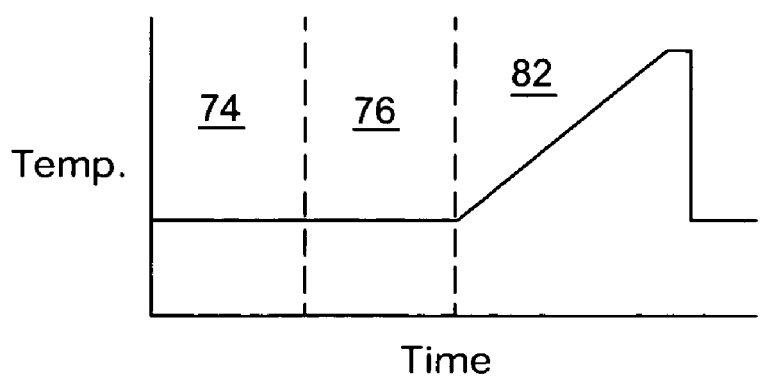
Figure 21:
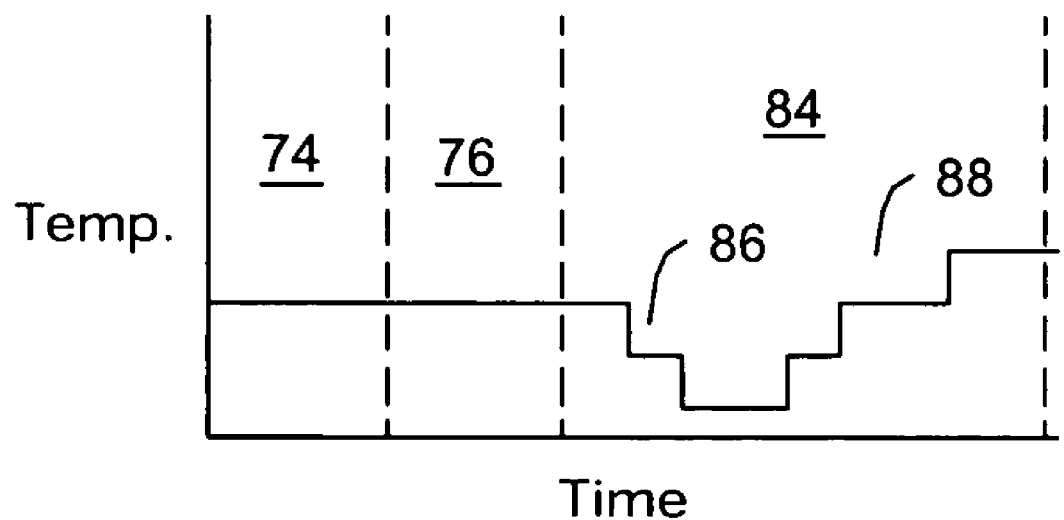
Figure 22:
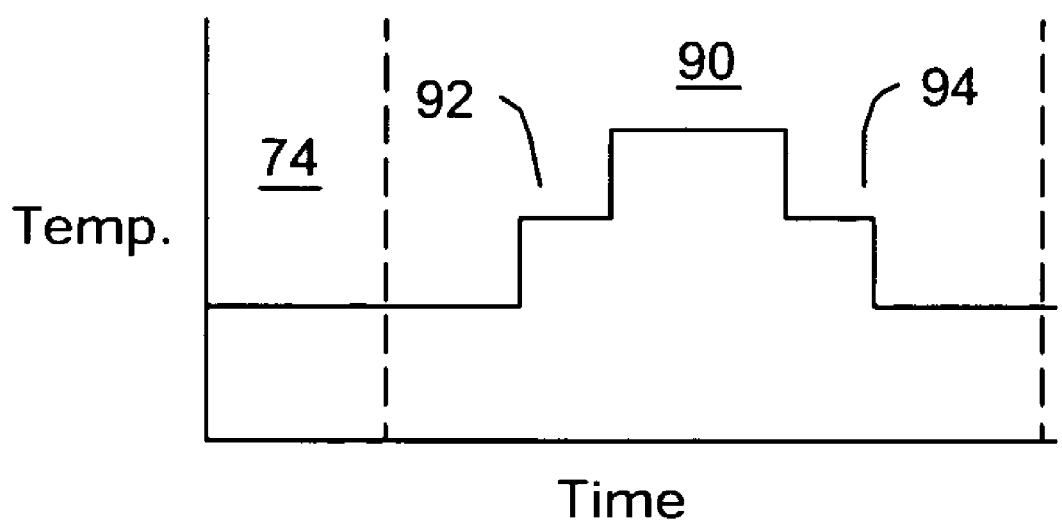

An illustrative controller 64 is shown in FIG. 17, which may be used with detector systems 10, 28 and 42 and combinations and/or variations thereof. The illustrative controller 64 is configured and adapted to communicate with energy source 14 and detector 16. Controller 64 may also be configured and adapted to communicate with a user through a user interface 65. Controller 64 can also be configured and adapted to communicate with thermoelectric device 30, a temperature sensor 34, and sometimes a humidity sensor 67. As such, the illustrative controller 64 includes an energy source control block 66, a detector control block 68, a thermoelectric device control block 70, a temperature sensor block 72, and in some cases a humidity sensor 67.

Energy source control block 66 can include the programming necessary to operate energy source 14. In some embodiments, energy source control block 66 can provide energy source 14 with a simple ON or OFF command. Energy source 14 can in some embodiments provide energy source control block 66 with confirmation that the ON or OFF command has been received and has in fact been enacted. In some cases, the confirmation of the commands issued by energy source control block 66 and resulting actions by energy source 14 can be communicated to the user through user interface 65.

Alternatively, or in addition, energy source control block 66 can provide energy source 14 with additional or other commands such as POWER LEVEL, WAVELENGTH and DURATION, among others. POWER LEVEL, WAVELENGTH and DURATION instruct energy source 14 to provide energy at a particular power level, particular wavelength and for a particular period of time, respectively. In some embodiments, energy source control block 66 can tailor the operation of energy source 14 using a variety of different profiles.

Detector control block 68 can include the programming necessary to operate detector 16. In some embodiments, detector control block 68 can provide detector 16 with a simple ON or OFF command. Detector 16 can in some embodiments provide detector control block 68 with confirmation that the ON or OFF command has been received and has in fact been enacted. In some cases, confirmation of the commands issued by detector control block 68 and resulting actions by detector 16 can be communicated to the user through user interface 65.

Alternatively, or in addition, detector control block 68 can provide a variety of additional or other commands to detector 16. For example, if detector 16 is capable of being adjusted to detect multiple wavelengths, detector control block 68 can issue a WAVELENGTH command that instructs detector 16 to adjust to a particular wavelength or range of wavelengths. This can be particularly useful if, for example, detector 16 includes one or more Fabry-Perot filters that can be tuned to a particular wavelength through the use of piezoelectric or electrostatic actuation.

As noted above, detector 16 can include a plurality of pixels that are each capable of being adjusted to detect a selected wavelength or range of wavelengths. In such embodiments, detector control block 68 may provide detector 16 with instructions to assign each pixel or a set of pixels to different wavelengths. In some embodiments, detector control block 68 may instruct detector 16 to retain a spatially resolved image of light such as induced fluorescence emitted by the sample particles retained by sample collection surface 20. In such embodiments, detector control block 68 can instruct detector 16 to assign each pixel to a particular location on sample collection surface 22 (FIG. 1), and in some cases, each pixel can be scanned across a range of wavelengths.

Thermoelectric device control block 70 can, in conjunction with temperature sensor block 72, provide thermoelectric device 30 with instructions or control signals to heat and/or cool sample collection surface 22 (FIG. 1) to one or several different temperatures, depending on a desired temperature profile. Depending on what materials are present in the sample being tested, it may be useful to test the sample at more than one temperature. For example, some materials will fluoresce more intensely or will experience a spectrum shift at one temperature more than at another temperature.

Temperature can also be used for selectivity, particularly if a sample being tested includes several different materials and/or particle types. For example, and as noted above, if the sample includes proteins, relatively small temperature changes (perhaps on the order of 10° C.) can cause the proteins to at least partially denature (change or lose their three dimensional shape) and thus can significantly change or even eliminate the induced fluorescence. Some materials of interest can contain water and in fact may require the presence of water. NADH, which is a molecule involved in cellular energy production, requires water. Simply heating the sample to greater than 100° C. will evaporate the water, and eliminate or reduce the induced fluorescence from the NADH. Other substances, including anthrax, may withstand higher temperatures, and thus heat can be used to remove the induced fluorescence from other materials to help confirm the presence of anthrax in the particle sample.

When the sample is in a dry state, the denaturation temperature of proteins can be highly sensitive to humidity. Thus, and as discussed above with respect to FIG. 4 above, the sample collection surface 22 may be provided in a sample collection chamber 31, and the humidity around the sample can be controlled by a humidity controller 33. While the humidity controller 33 may include a saturated salt solution or the like placed in the sample collection chamber 31, it is contemplated that a more active control system may be used. For example, a humidity sensor 67 (see FIG. 17) may be provided in the sample collection chamber 31, and the controller 64 may actively increase or decrease the water content in the sample collection chamber 31 by, for example activating a humidifier and/or dehumidifier (not shown), if desired. While the humidity in the sample collection chamber 31 is preferably maintained at a relatively constant humidity level, it is contemplated that the controller 64 may vary the humidity in the sample collection chamber 31, sometimes in accordance with a humidity profile, which in some cases, may provide additional discrimination, if desired. Also, it is contemplated that controller 64 may control and sometimes vary the PH level at the sample collection surface 22, which in some cases, may also help provide discrimination, if desired. It is also contemplated that the controller 64 may cause certain chemicals to be selectively added to the sample, which may help denature proteins to provide additional discrimination.

FIGS. 18-22 illustrate several possible temperature profiles in accordance with the present invention. The temperature profile used for examining a particular sample can be programmed into thermoelectric device control block 70 (FIG. 17). In some embodiments, each temperature setting of the temperature profile can be individually inputted by a user through user interface 65 (FIG. 17) in response to the fluorescence detected (if any) at a particular temperature. In other embodiments, the temperature profiles can be uploaded to the thermoelectric device control block 70 during initialization or some later time.

FIG. 18 shows a temperature profile that includes a profile portion 74 that can provide an opportunity take a reference reading to ascertain any background fluorescence provided by the sample collection surface 22 (FIG. 1) at a first constant temperature. After the sample is provided to the sample collection surface, fluorescence (if any) may be detected at a constant temperature as illustrated in profile portion 76. The temperature can be ambient temperature, or can represent the result of either heating or cooling the sample prior to testing. In some embodiments, the sample can be tested more than once at the given temperature. Subsequent to testing, and as shown in FIG. 18, the sample may be heated to a temperature sufficient to at least substantially reduce or eliminate any induced fluorescence provided by the sample, as seen in profile portion 78. This may be a temperature that kills and/or burns the particles in the sample.

FIG. 19 shows a temperature profile that begins with profile portion 74 and profile portion 76 as described with respect to FIG. 18. This temperature profile, however, also includes a profile portion 80 that includes several step-wise temperature increases. In this embodiment, energy is directed towards the sample by the energy source 14 and at least some of the induced fluorescence is detected by detector 16. The temperature is increased, and the sample is again excited by the energy source 14, and at least some of any induced fluorescence is detected by detector 16. In some embodiments, each of the temperature set points can be programmed into thermoelectric device control block 72 (FIG. 17), while in other embodiments each temperature set point can be individually input into thermoelectric device control block 72 (FIG. 17) by a user. This temperature profile may be particularly suitable for determining how many different proteins there are in the sample.

FIG. 20 shows another illustrative temperature profile that begins with profile portions 74 and 76, as described with respect to FIG. 18. This temperature profile, however, also includes a profile portion 82 that includes a linear or substantially linear temperature increase over time. In some embodiments, energy is continuously directed towards the sample by energy source 14, thereby exciting the sample, and at least some of any induced fluorescence is detected while the temperature increases. In other embodiments, energy is incrementally directed towards the sample by energy source 14, and at least some of any induced fluorescence is detected, and then a finite period of time passes (while the temperature increases) before energy is once again directed towards the sample. This temperature profile may be particularly suitable for detecting a characteristic denaturation temperature of specific proteins in the sample.

FIG. 21 shows another illustrative temperature profile that begins with profile portions 74 and 76 as discussed above. This temperature profile, however, also includes a profile portion 84 that includes one or several downward temperature steps in profile portion 86 followed by one or several upward temperature steps in profile portion 88. In the illustrative temperature profile of FIG. 21, the sample is initially illuminated and at least some of any induced fluorescence is detected at a first temperature while in profile portion 86. The sample is then cooled, which may cause changes in the sample and thus change any induced fluorescence. For example, as discussed previously, proteins can be quite sensitive to relatively small temperature changes up or down. The sample can be retested at the same temperature again in profile portion 88, if desired. Any changes in induced fluorescence when retested may be useful in helping to identify the particles in the particle sample. This temperature profile may be particularly suitable for identifying intermediate state of protein folding.

FIG. 22 shows another illustrative temperature profile that begins with profile portion 74 as discussed previously. This temperature profile, however, also includes a profile portion 90 that includes one or several upward steps in temperature in profile portion 92 followed by one or several downward temperature steps in profile portion 94.

In some embodiments, it can be useful to test a sample at a particular temperature while in profile portion 92. The temperature can be increased, which can cause changes in the sample as previously discussed. The sample can be retested at the same particular temperature again in profile portion 94, if desired. Any changes in induced fluorescence when retested may be useful in helping to identify the particles in the particle sample. This temperature profile may be used to, for example, determining any renaturation of proteins.

FIGS. 23-31 are flow diagrams illustrating illustrative methods that can be performed using detection systems 10, 28 and 42 controlled by controller 64 (FIG. 17). These methods are intended merely to illustrate particular embodiments and particular examples, but are not to be construed as limiting the invention in any manner.

During the methods shown in FIGS. 23-31, it is contemplated that the humidity around the sample may also be controlled by, for example, a humidity controller 33. In some embodiments, the humidity is maintained at a relatively constant level, while in others, the humidity may be varied sometimes along a humidity profile. The humidity profile may, for example, work in conjunction with the temperature profile to provide additional discrimination, if desired.

Alternatively, or in addition, it is contemplated that the PH level at the sample may be controlled, sometimes at a constant value and sometimes along a PH profile. The PH profile may, for example, work in conjunction with the temperature profile and/or humidity profile to provide additional discrimination, if desired. It is also contemplated that certain chemicals may be selectively added to the sample, which may help denature proteins to provide additional discrimination, if desired. In some cases, the chemicals may be added in accordance with a chemical profile, which may for example, work in conjunction with the temperature profile, humidity profile, and/or PH profile to provide additional discrimination, if desired.

Figure 23:
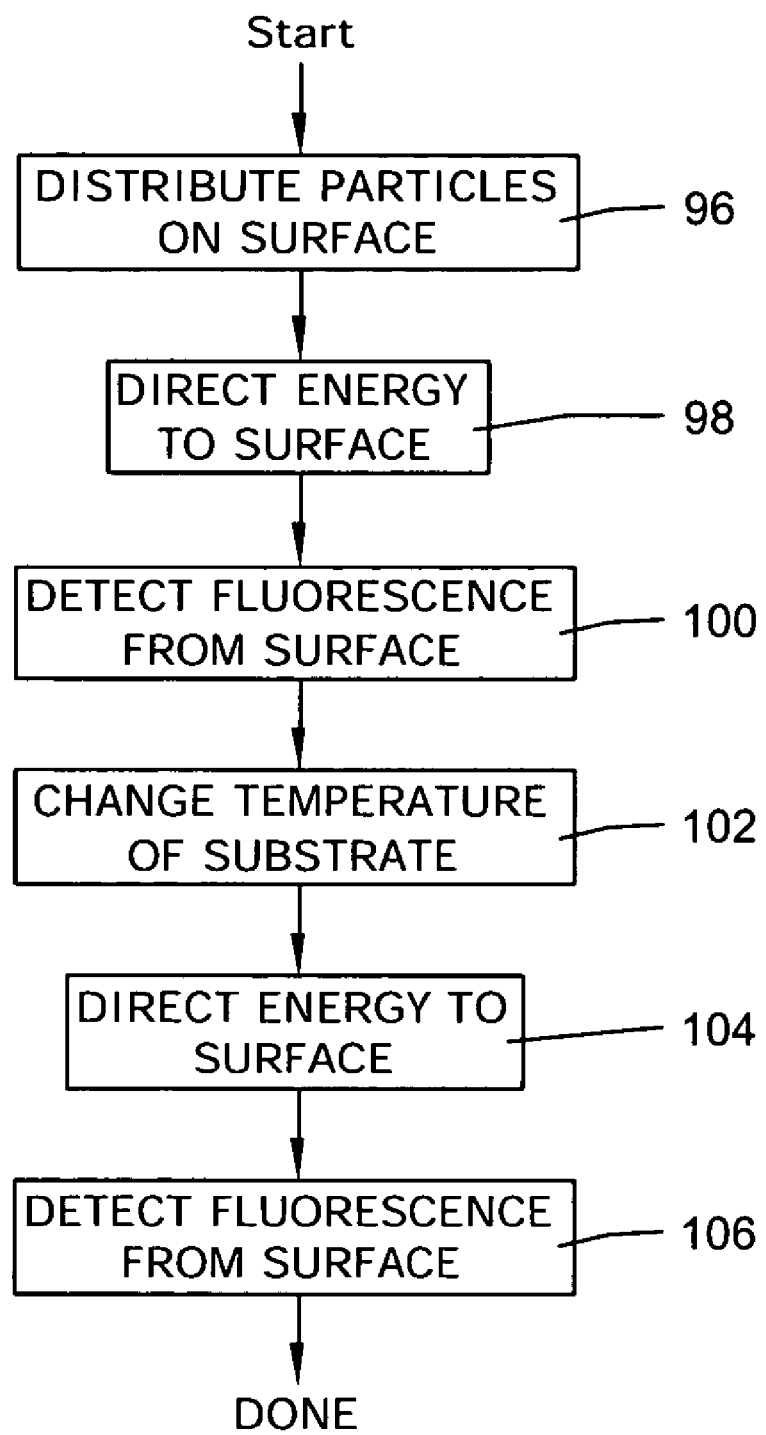
FIG. 23 is a flow diagram showing an illustrative method that may be implemented by the controller of FIG. 17.

Turning now specifically to FIG. 23, the illustrative method begins by distributing particles onto sample collection surface 22 (FIG. 1), as outlined at block 96. As discussed previously, the step of distributing particles can be carried out in a variety of ways. At block 98, energy is directed towards the particle sample on the sample collection surface 22. In some embodiments, a command signal from energy source control block 66 (FIG. 17) may be provided to energy source 14 (FIG. 17). In some embodiments, and if desired, user interface 65 (FIG. 17) can provide the user with confirmation.

At block 100, at least some of any induced fluorescence is detected by detector 16 (FIG. 17), which has been activated and if necessary tuned by a command signal from detector control block 68 (FIG. 17) to detector 16 (FIG. 17). A signal or data representing any detected fluorescence, and in some cases as well as any important operating parameters associated with detector 16, may be outputted to the controller and stored for later analysis, and/or provided to the user interface 65 (FIG. 17), if desired.

The temperature of sample collection surface 22 (FIG. 1) is then changed at block 102. Thermoelectric device control block 70 (FIG. 17) can send a signal to activate thermoelectric device 30 (FIG. 17) to either raise or lower the temperature of sample collection surface 22 (FIG. 1). The temperature may be changed in accordance with a temperature profile, such as the temperature profiles discussed above. A signal from temperature sensor 34 (FIG. 17) may be returned to temperature sensor block 72 (FIG. 17), which may be used to provide feedback control to thermoelectric device control block 70 (FIG. 17).

Once the temperature of sample collection surface 22 (FIG. 1) reaches a particular target set point as determined in some embodiments by the temperature profile programmed into thermoelectric device control block 70 (FIG. 17), the sample can again be tested. At block 104, energy is directed from energy source 14 (FIG. 17) to the sample on sample collection surface 22 (FIG. 1). At least some of any induced fluorescence is then detected by detector 16 (FIG. 17), as referenced at block 106. As before, a signal or data representing any detected fluorescence, and in some cases as well as any important operating parameters associated with detector 16, may be outputted to the controller and stored for later analysis, and/or provided to the user interface 65 (FIG. 17), if desired.

Figure 24:
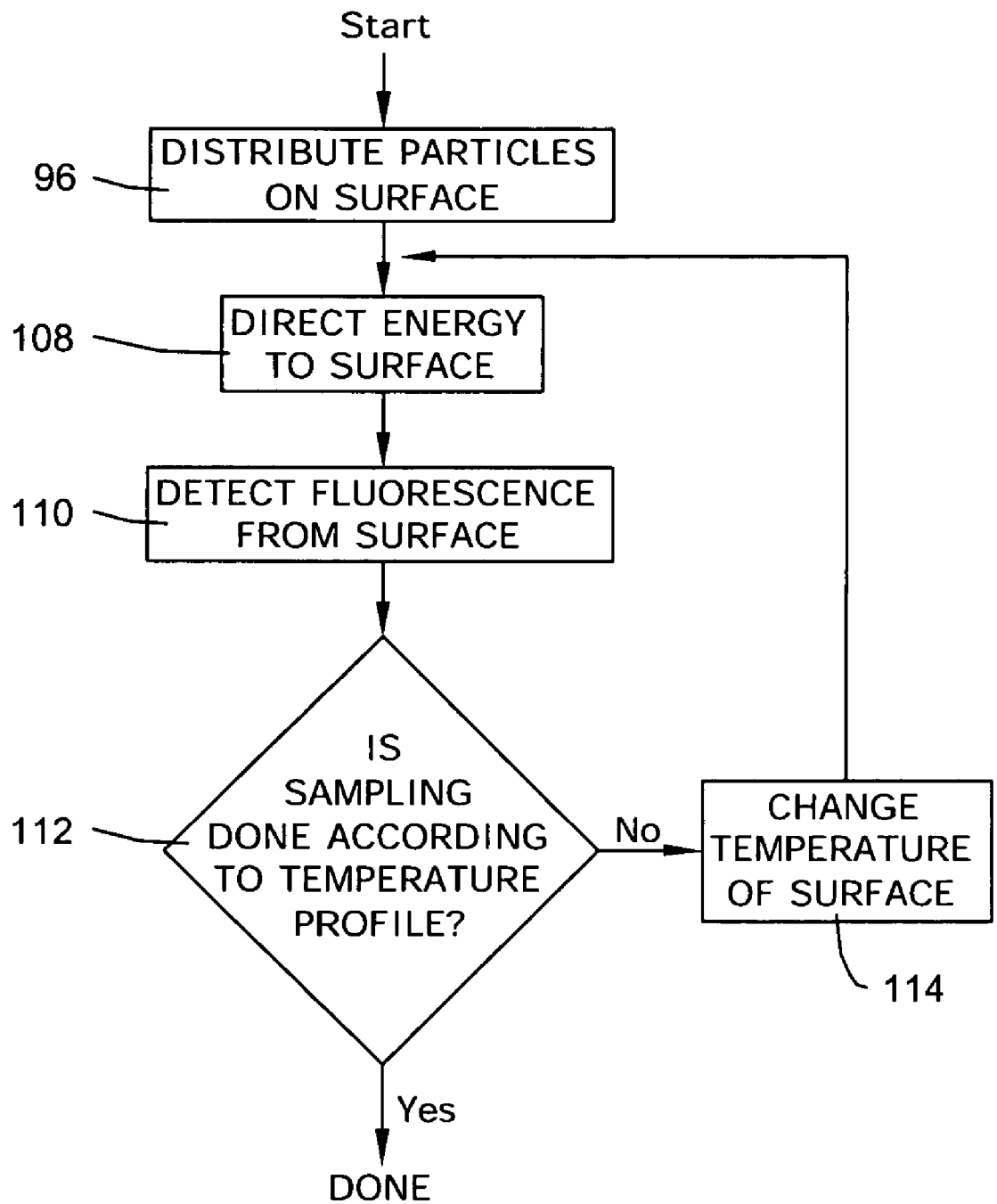
FIG. 24 is a flow diagram showing an illustrative method that may be implemented by the controller of FIG. 17.

FIG. 23 shows an illustrative algorithm in which the sample is tested at two distinct temperatures. FIG. 24, however, shown an illustrative algorithm in which the sample is tested at any number of temperatures. The illustrative algorithm begins at block 96, at which particles are distributed onto sample collection surface 22 (FIG. 1) using any of a variety of methods. At block 108, energy is directed from energy source 14 (FIG. 17) to sample collection surface 22 (FIG. 1), some times as a result of a command signal from energy source control block 66 (FIG. 17) to energy source 14 (FIG. 17).

At block 110, at least some of any induced fluorescence is detected by detector 16 (FIG. 17), which has been activated and in some cases tuned to a particular wavelength band or across a range of wavelengths by a command signal from detector control block 68 (FIG. 17) to detector 16 (FIG. 17). A signal or data representing any detected fluorescence, and in some cases as well as any important operating parameters associated with detector 16, may be outputted to the controller and stored for later analysis, and/or provided to the user interface 65 (FIG. 17), if desired. Control is then passes to decision block 112, at which controller 64 (FIG. 17) determines if testing according to the programmed temperature profile is complete. If testing is complete, the algorithm is exited.

If testing is not complete, control passes to block 114, at which point thermoelectric device control block 70 (FIG. 17) sends a signal to activate thermoelectric device 30 (FIG. 17) to either raise or lower the temperature of sample collection surface 22 (FIG. 1). A signal from temperature sensor 34 (FIG. 17) may be returned to temperature sensor block 72 (FIG. 17), which in turn provides feedback control to thermoelectric device control block 70 (FIG. 17). Once the temperature of sample collection surface 22 (FIG. 1) reaches a particular target set point, the sample can again be tested as shown at block 108.

Figure 25:
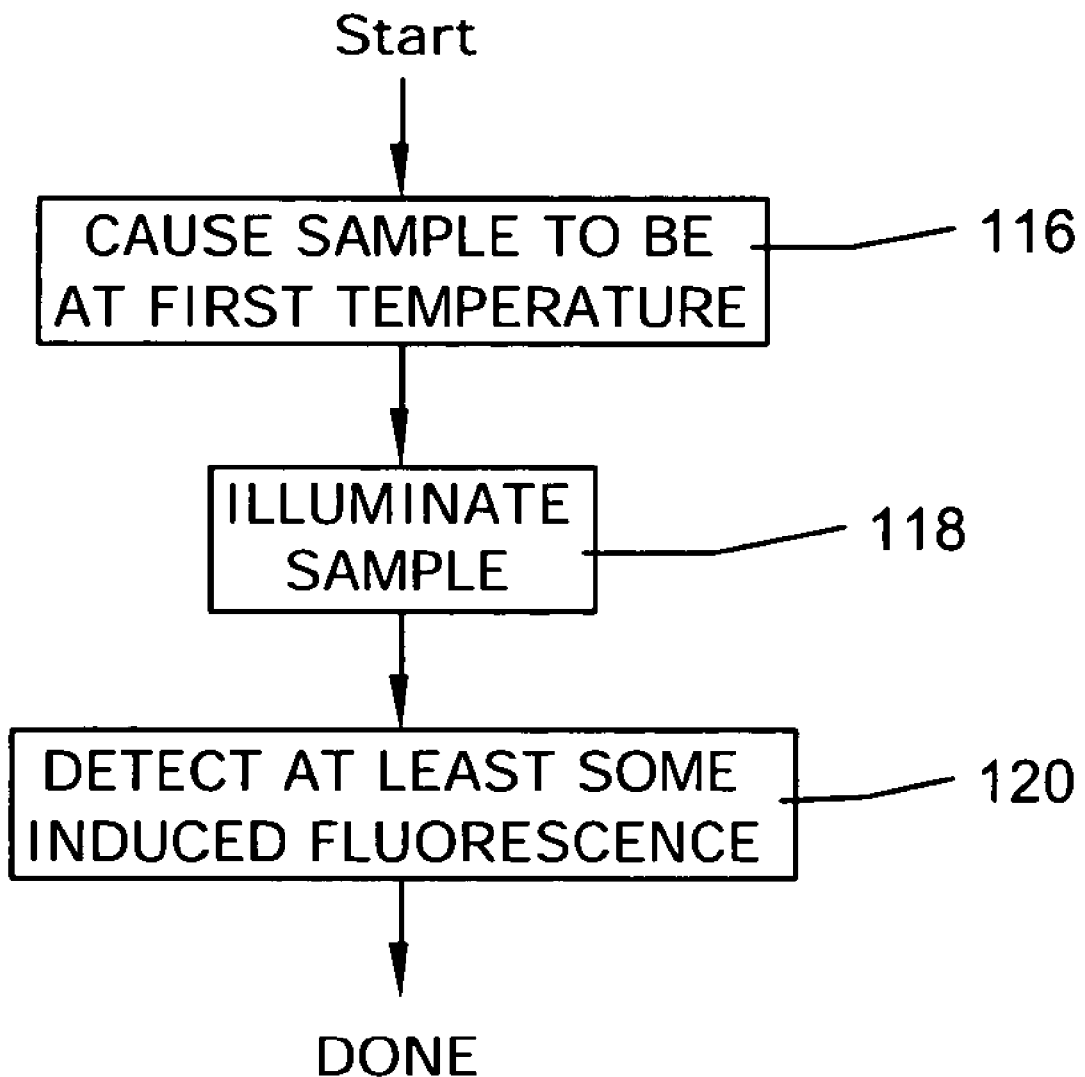
FIG. 25 is a flow diagram showing an illustrative method that may be implemented by the controller of FIG. 17.

Turning now to FIG. 25, an illustrative algorithm is shown in which a sample is tested at a single temperature. Control begins at block 116, wherein controller 64 (FIG. 17) causes the sample to be at a first temperature. In some embodiments, thermoelectric device control block 70 (FIG. 17) sends a signal to activate thermoelectric device 30 (FIG. 17) to either raise or lower the temperature of the sample to achieve the first temperature. A signal from temperature sensor 34 (FIG. 17) may be returned to temperature sensor block 72 (FIG. 17), which in turn may provide feedback control to thermoelectric device control block 70 (FIG. 17).

Once the sample temperature reaches the first temperature set point, control passes to block 118, at which point the sample is illuminated by energy source 14 (FIG. 17). At block 120, detector 16 (FIG. 17) is activated by a signal from detector control block 68 (FIG. 17) and detector 16 (FIG. 17) detects at least some of any induced fluorescence.

Figure 26:
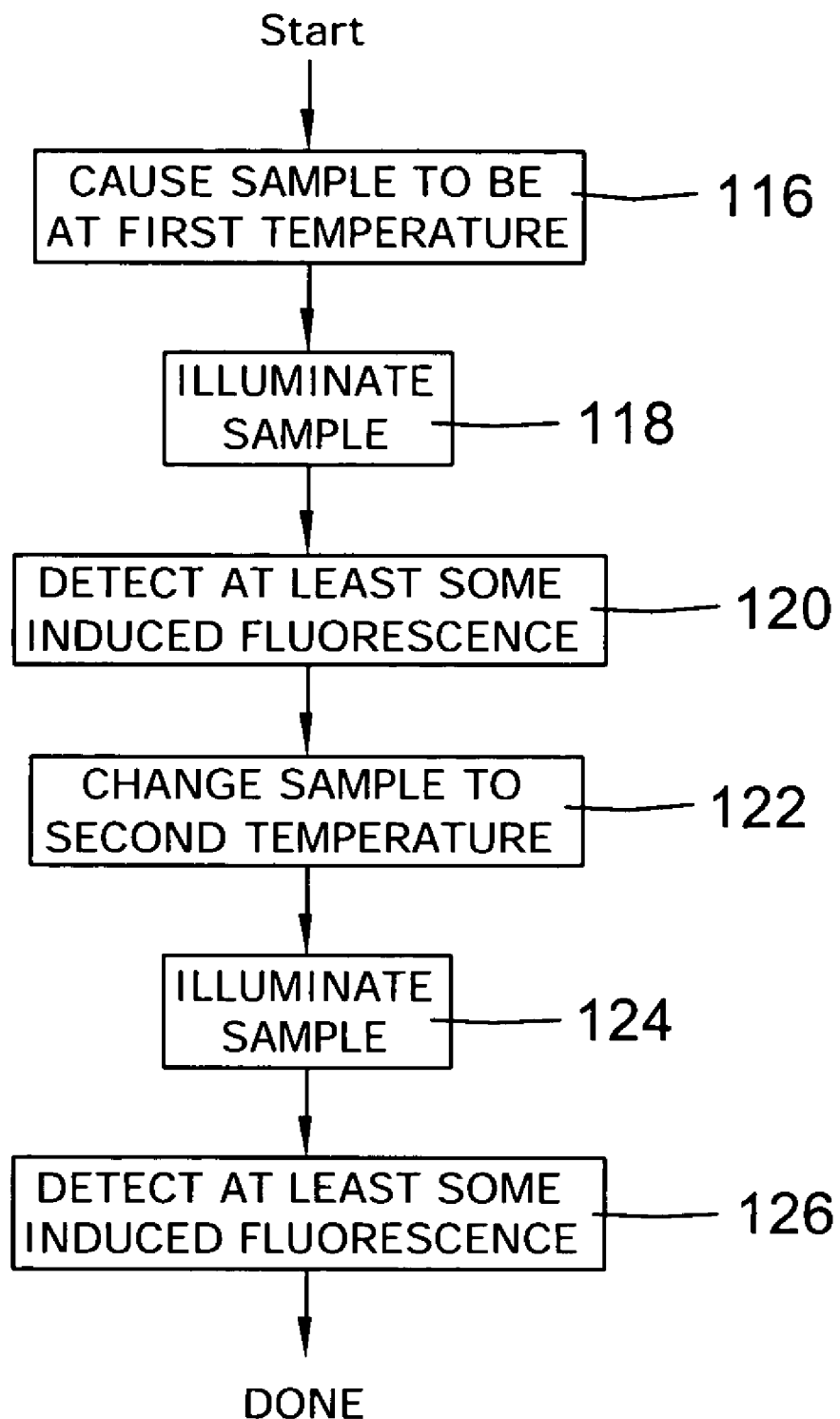
FIG. 26 is a flow diagram showing an illustrative method that may be implemented by the controller of FIG. 17.

FIG. 26 illustrates an expansion of this algorithm, as blocks 116, 118 and 120 are identical to those of FIG. 25. However, in FIG. 26, control passes from block 120 to block 122, at which point thermoelectric device control block 70 (FIG. 17) sends a signal to activate thermoelectric device 30 (FIG. 17) to change the temperature of the sample to a second temperature set point. As discussed previously, temperature sensor 34 (FIG. 17) may operate in conjunction with temperature sensor block 72 (FIG. 17) and thermoelectric device control block 70 (FIG. 17) to provide the desired temperature.

Once the second temperature set point has been reached, control passes to block 124, at which point the sample is illuminated once again by energy source 14 (FIG. 17), often activated by a command signal from energy source control block 66 (FIG. 17) to energy source 14 (FIG. 17). At block 126, detector 16 (FIG. 17) is activated by a signal from detector control block 68 (FIG. 17), and detector 16 (FIG. 17) detects at least some of any induced fluorescence.

Figure 27:
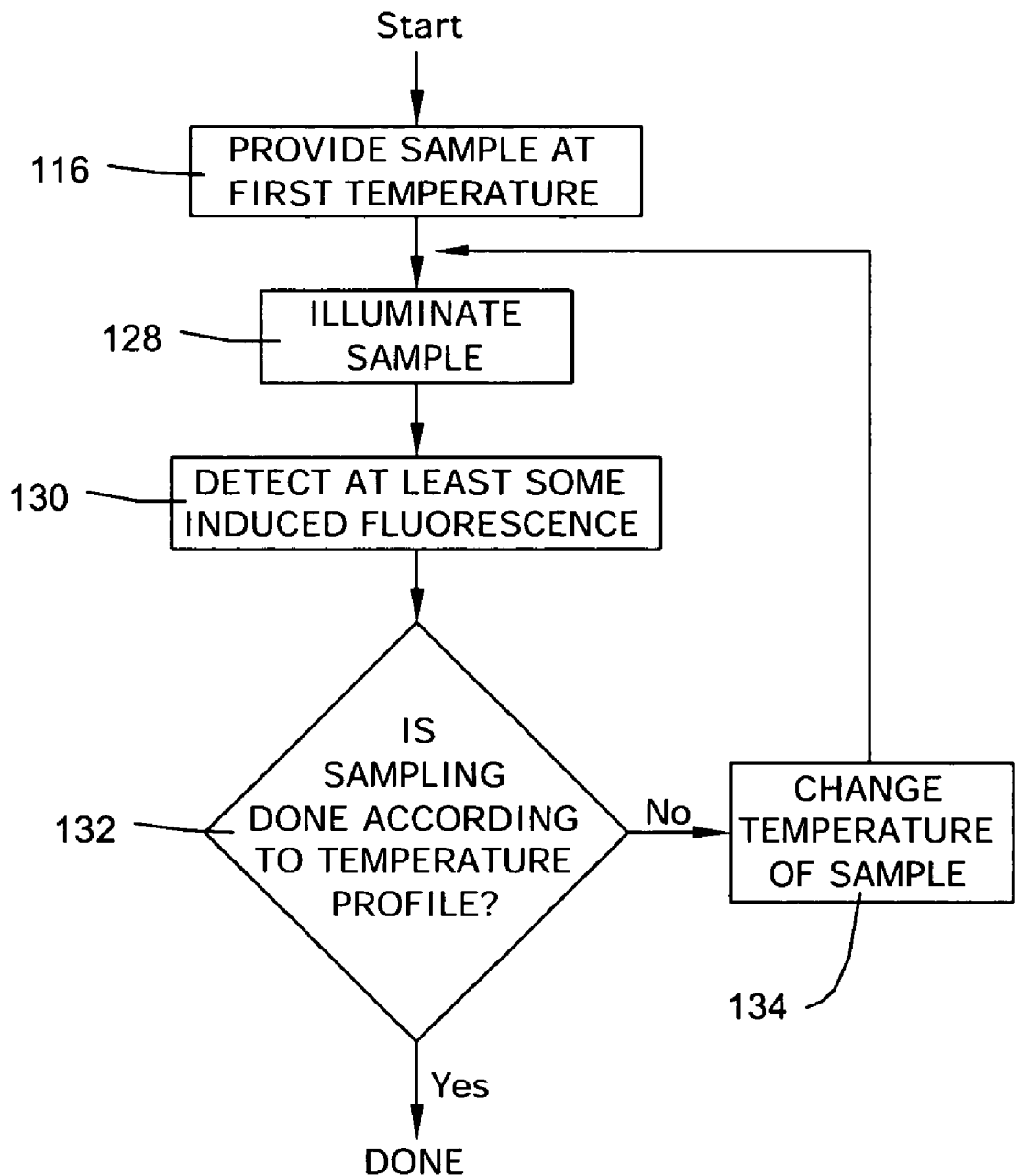
FIG. 27 is a flow diagram showing an illustrative method that may be implemented by the controller of FIG. 17.

FIG. 27 represents a continuation of this algorithm in which the sample is tested at a number of temperature set points. Control begins at block 116, with controller 64 (FIG. 17) causing the sample to be at a first temperature. Thermoelectric device control block 70 (FIG. 17) sends a signal to activate thermoelectric device 30 (FIG. 17) to either raise or lower the temperature of the sample. A signal from temperature sensor 34 (FIG. 17) may be returned to temperature sensor block 72 (FIG. 17), which in turn provides feedback control to thermoelectric device control block 70 (FIG. 17).

Once the sample temperature reaches the first temperature set point, control passes to block 128, at which point the sample is illuminated by energy source 14 (FIG. 17), sometimes activated by a command signal from energy source control block 66 (FIG. 17) to energy source 14 (FIG. 17). At block 130, detector 16 (FIG. 17) is activated by a signal from detector control block 68 (FIG. 17) and detector 16 (FIG. 17) detects at least some of any induced fluorescence.

Control then passes to decision block 132, where controller 64 (FIG. 17) determines if testing according to the temperature profile has been completed. If testing is not yet complete, control passes to block 134, at which point thermoelectric device control block 70 (FIG. 17) sends a signal to activate thermoelectric device 30 (FIG. 17) to change the temperature of the sample to a new temperature. As discussed previously, temperature sensor 34 (FIG. 17) may operate in conjunction with temperature sensor block 72 (FIG. 17) and thermoelectric device control block 70 (FIG. 17). Once the new temperature has been reached, control passes back to block 128 and the sample is illuminated once again.

Figure 28:
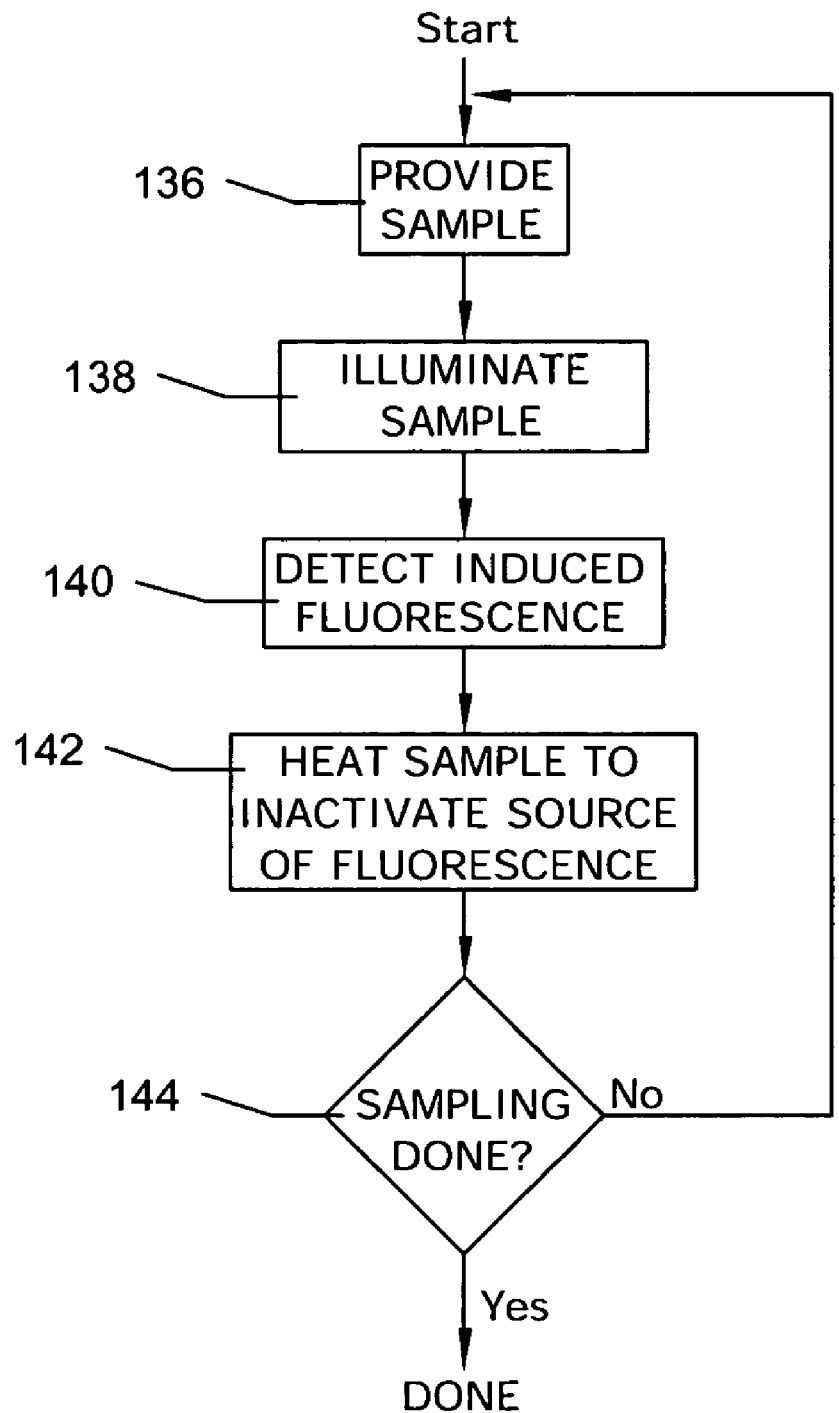
FIG. 28 is a flow diagram showing an illustrative method that may be implemented by the controller of FIG. 17.

Turning now to FIG. 28, another illustrative algorithm is shown. A sample is provided at block 136. As discussed above, a sample can be provided in a variety of different manners, including using sample collector 44 (FIG. 5). Control passes to block 138, where the sample is illuminated by energy source 14 (FIG. 17), sometimes activated by a command signal from energy source control block 66 (FIG. 17) to energy source 14 (FIG. 17). At block 140, detector 16 (FIG. 17) is activated, sometimes by a signal from detector control block 68 (FIG. 17), and detector 16 (FIG. 17) detects at least some of any induced fluorescence.

Control passes to block 142, where the sample is heated to a temperature sufficient to at least partially, substantially, or completely inactivate any source of induced fluorescence. To accomplish this, thermoelectric device control block 70 (FIG. 17) may send a signal to activate thermoelectric device 30 (FIG. 17) to heat the sample to an elevated temperature. As discussed previously, temperature sensor 34 (FIG. 17) may operate in conjunction with temperature sensor block 72 (FIG. 17) and thermoelectric device control block 70 (FIG. 17) to help achieve the desired elevated temperature. The elevated temperature used to inactivate any induced fluorescence can vary depending on the materials being tested. In some embodiments, the elevated temperature can range from about 100° C. to about 600° C. or higher.

Next, control passes to decision block 144, where controller 64 (FIG. 17) determines if sampling is complete. If sampling is not complete, control passes back to block 136, wherein a new sample is provided to the sample collection surface.

Figure 29:
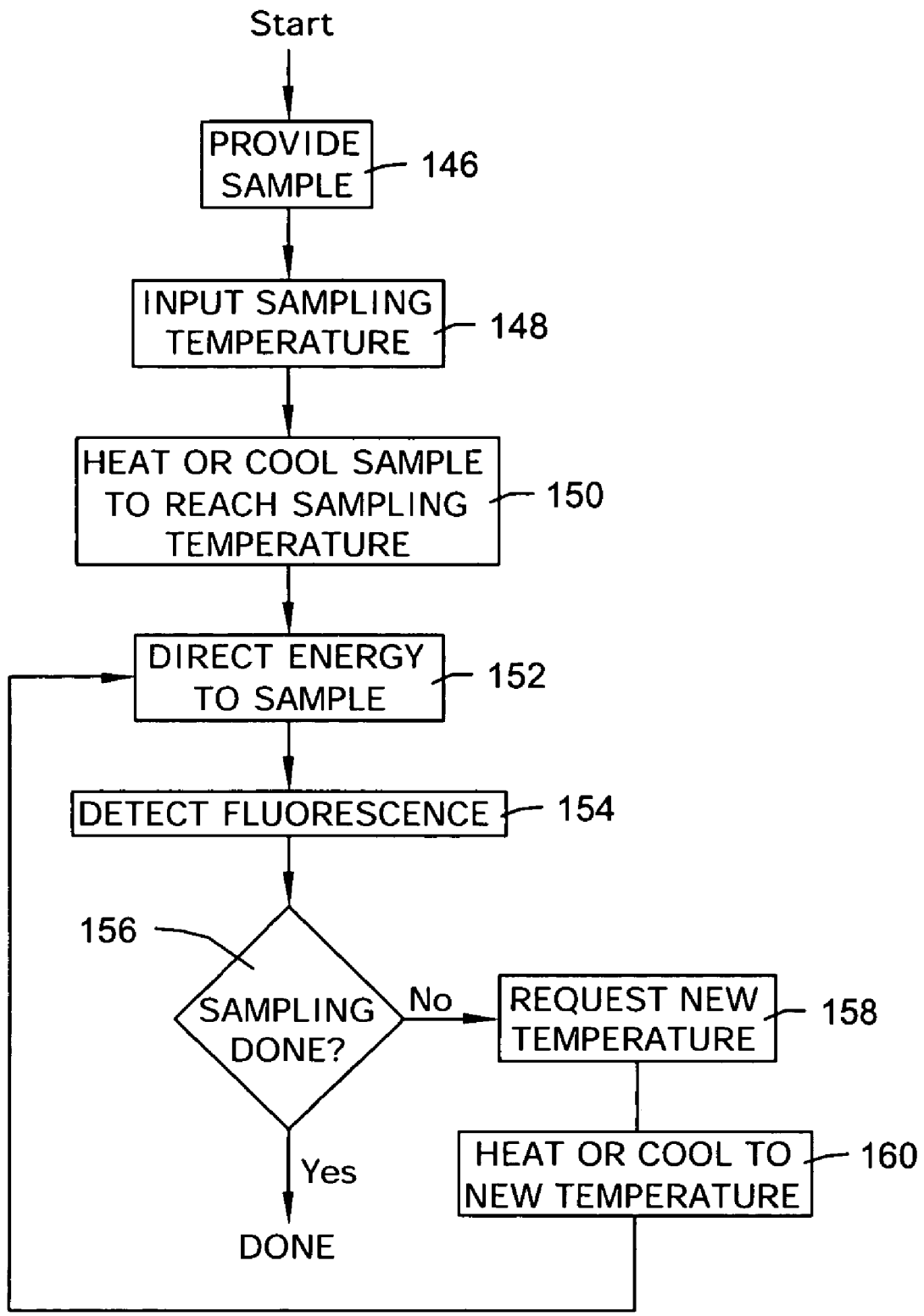
FIG. 29 is a flow diagram showing an illustrative method that may be implemented by the controller of FIG. 17.

FIG. 29 illustrates another illustrative algorithm in which a user provides controller 64 (FIG. 17) with appropriate testing parameters through user interface 65 (FIG. 17). A sample is provided at block 146, using any suitable method or technique. Control passes to block 148, where controller 64 (FIG. 17) asks the user to input a sampling temperature through the user interface 65 (FIG. 17). Once the sampling temperature has been entered, control passes to block 150, where thermoelectric device control block 70 (FIG. 17) sends a signal to activate thermoelectric device 30 (FIG. 17) to heat or cool the sample to the inputted sample temperature. As discussed previously, temperature sensor 34 (FIG. 17) may operate in conjunction with temperature sensor block 72 (FIG. 17) and thermoelectric device control block 70 (FIG. 17) to help achieve the desired temperature.

Next, control passes to block 152, where energy from energy source 14 (FIG. 17) is directed to the sample by energy source 14 (FIG. 17), sometimes activated by a command signal from energy source control block 66 (FIG. 17) to energy source 14 (FIG. 17). At block 154, detector 16 (FIG. 17) is activated, sometimes by a signal from detector control block 68 (FIG. 17), and detector 16 (FIG. 17) detects at least some of any induced fluorescence.

Control passes to decision block 156, where controller 64 (FIG. 17) determines via its programming or by asking the user for additional input if sampling is complete. If sampling is not complete, control passes to block 158. At block 158, controller 64 (FIG. 17) asks the user to input a new sample temperature. Control passes to block 160, at which point thermoelectric device control block 70 (FIG. 17) sends a signal to activate thermoelectric device 30 (FIG. 17) to heat or cool the sample to the inputted sample temperature. As discussed previously, temperature sensor 34 (FIG. 17) may operate in conjunction with temperature sensor block 72 (FIG. 17) and thermoelectric device control block 70 (FIG. 17) to achieve the desired temperature. Once the sample has been heated or cooled to reach the newly inputted sample temperature set point, control passes back to block 152.

Figure 30:
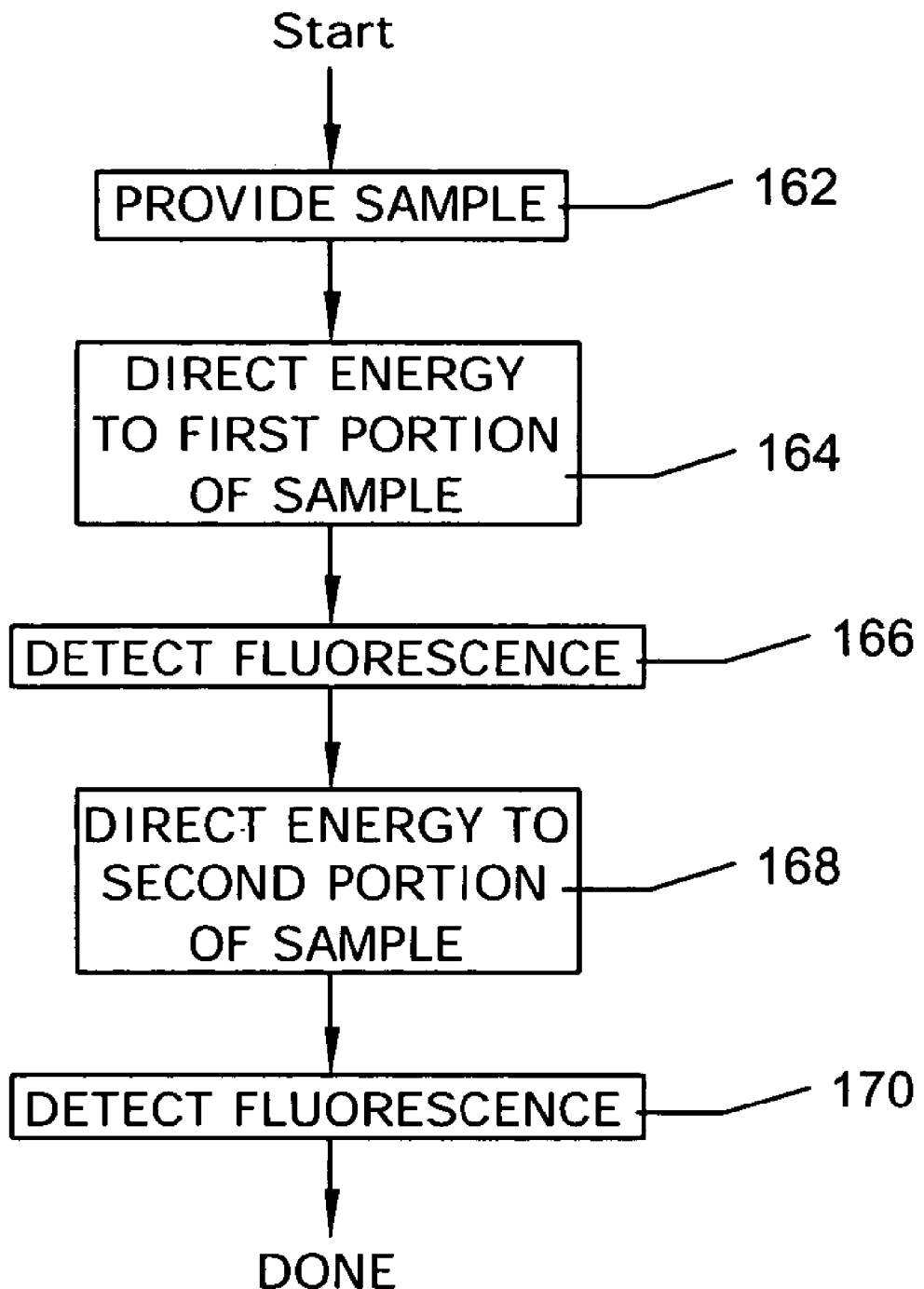
FIG. 30 is a flow diagram showing an illustrative method that may be implemented by the controller of FIG. 17.
Figure 31:
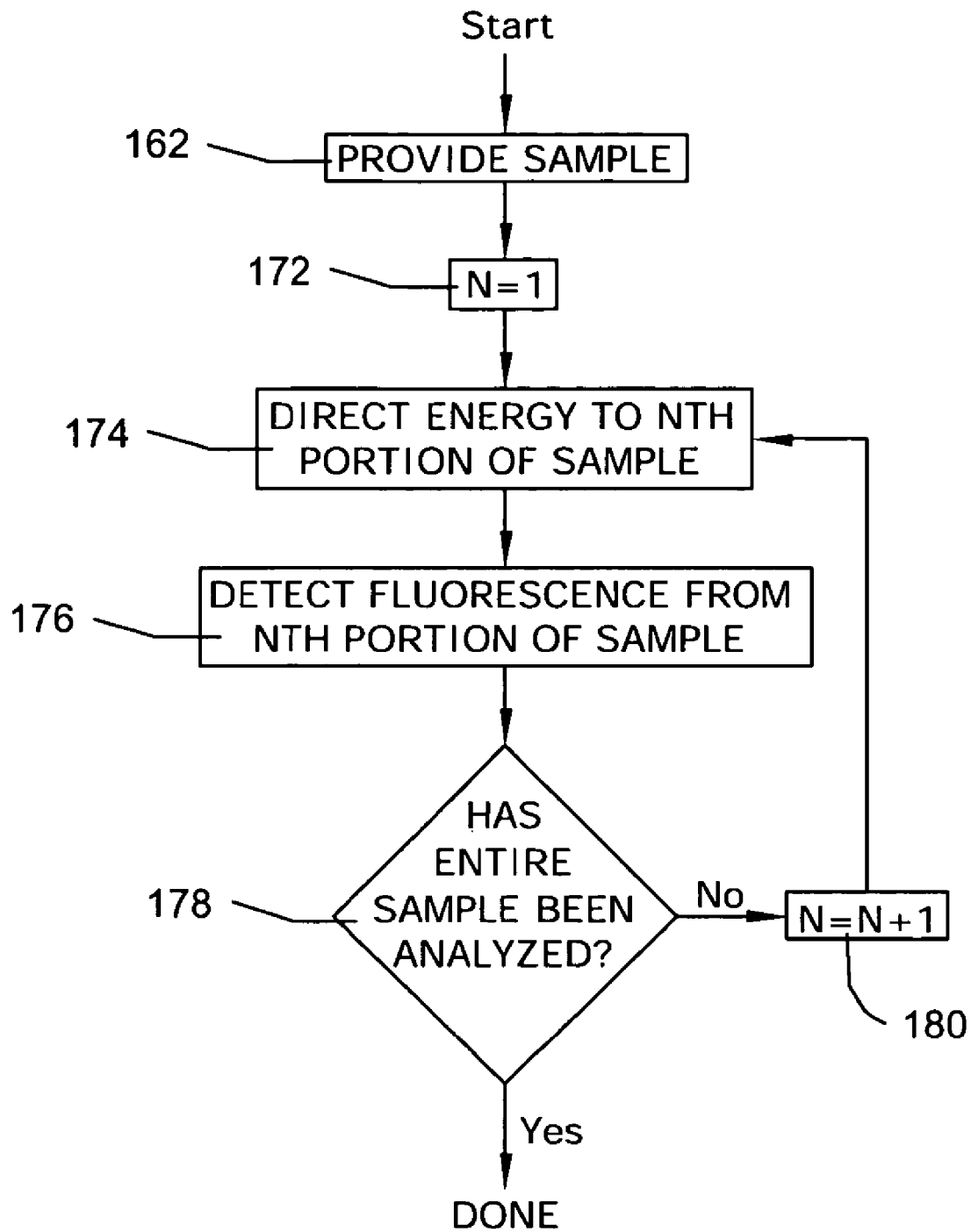
FIG. 31 is a flow diagram showing an illustrative method that may be implemented by the controller of FIG. 17.

FIGS. 30 and 31 show illustrative algorithms in which only a portion of a sample on the sample collection surface is tested at any given time. This can be useful if, for example, the sample is particularly large, or if energy source 14 (FIG. 17) provides energy such as a light beam that is too focused to illuminate substantially all of the sample simultaneously. In FIG. 30, the algorithm begins at block 162, with providing a sample.

Control passes to block 164, where energy is directed towards a first portion of the sample. As indicated above, energy source 14 (FIG. 17) may be activated by a command signal from energy source control block 66 (FIG. 17) to energy source 14 (FIG. 17). The command signal from energy source control block 66 (FIG. 17) may, in the illustrative embodiment, include instructions to energy source 14 (FIG. 17) regarding which portion of the sample to direct energy towards. In some embodiments, energy source control block 66 (FIG. 17) may provides aiming instructions to energy source lens 38 (FIG. 4). That is, rather than moving the energy source 14 and/or sample collection surface, or in addition to moving the energy source 14 and/or sample collection surface, it is contemplated that the energy source lens 38 may be moved to provide a level of beam steering.

At block 166, detector 16 (FIG. 17) is activated, sometimes by a signal from detector control block 68 (FIG. 17), and detector 16 (FIG. 17) detects at least some of any induced fluorescence. In some embodiments, detector control block 68 (FIG. 17) can provide command instructions to detector lens 40 (FIG. 4) regarding focusing, beam steering or the like, if desired.

Next, control passes to block 168, where energy is directed to a second portion of the sample. Again, energy source 14 (FIG. 17) may be activated or controlled by a command signal from energy source control block 66 (FIG. 17) to energy source 14 (FIG. 17). The command signal from energy source control block 66 (FIG. 17) can include instructions to energy source 14 (FIG. 17) and possibly energy source lens 38 (FIG. 4) regarding which portion of the sample to direct energy towards. At block 170, detector 16 (FIG. 17) is activated, sometimes by a signal from detector control block 68 (FIG. 17), and detector 16 (FIG. 17) detects at least some of any induced fluorescence.

FIG. 31 illustrates a related algorithm in which the sample is divided into a plurality of distinct portions, and each portion is illuminated separately. Control begins at block 162, where a sample is provided using any suitable technique such as sample collector 44 (FIG. 5). At block 172, a counter N is set equal to one. Control passes to block 174, where energy is directed to the Nth portion of the sample.

As noted above, energy source 14 may be activated by a command signal from energy source control block 66 (FIG. 17) to energy source 14 (FIG. 17). The command signal from energy source control block 66 (FIG. 17) can include instructions to energy source 14 (FIG. 17) and possibly energy source lens 38 (FIG. 4) regarding the particular portion of the sample to direct energy towards. Alternatively, or in addition, the sample collection surface may be moved, as noted above. At block 176, detector 16 (FIG. 17) is activated, sometimes by a signal from detector control block 68 (FIG. 17), and detector 16 (FIG. 17) detects at least some of any induced fluorescence emanating from the Nth portion of the sample.

Control passes to decision block 178, at which point controller 64 (FIG. 17) determines whether or not the entire or desired portion of the sample has been tested. If the entire or desired portion of the sample has not yet been tested, control passes to block 180. At block 180, counter N is incremented by one and control passes back to block 174.

The invention should not be considered limited to the particular examples described above, but rather should be understood to cover all aspects of the invention as set out in the attached claims. Various modifications, equivalent processes, as well as numerous structures to which the invention can be applicable will be readily apparent to those of skill in the art upon review of the instant specification.

What is claimed is:

1. A particle analyzer, comprising:
   a particle concentrator adapted to collect and concentrate particles found within an aerosol;
   a sample collection surface adapted to accept particles provided by the particle concentrator;
   a substrate adapted to mount the sample collection surface, the sample collection surface being at least partially thermally isolated from the substrate;
   an energy source that provides energy that is adapted to induce fluorescence in the particles held by the sample collection surface; and
   a detector adapted to detect the induced fluorescence.

2. The particle analyzer of claim 1, further comprising temperature modifying means thermally coupled to the sample collection surface.

3. The particle analyzer of claim 2, wherein the temperature modifying means comprises heating means.

4. The particle analyzer of claim 2, wherein the temperature modifying means comprises cooling means.

5. The particle analyzer of claim 2, wherein the energy source provides energy that induces at least some excitation fluorescence in a material of interest.

6. The particle analyzer of claim 2, wherein the detector is adapted and configured to detect excitation fluorescence while being at least substantially blind to reflective energy from the energy source.

7. The particle analyzer of claim 2, wherein the detector is adapted and configured to detect excitation fluorescence while being positioned at an angle relative to the sample collection surface such that reflective energy from the energy source does not impinge upon the detector.

8. The particle analyzer of claim 2, wherein the detector is sensitive to a plurality of wavelengths.

9. A particle analyzer, comprising:
   a particle concentrator adapted to collect and concentrate particles found within an aerosol;
   a sample collection surface adapted to accept particles provided by the particle concentrator, the sample collection surface comprising carbon nanotubes;
   an energy source that provides energy that is adapted to induce fluorescence in the particles held by the sample collection surface; and
   a detector adapted to detect the induced fluorescence.

10. A particle analyzer, comprising:
    a particle concentrator adapted to collect and concentrate particles found within an aerosol;
    a sample collection surface adapted to accept particles provided by the particle concentrator;
    an energy source that provides energy that is adapted to induce fluorescence in the particles held by the sample collection surface;
    an energy source lens adapted to direct the energy from the energy source to at least a portion of the sample collection surface; and
    a detector adapted to detect the induced fluorescence.

11. A particle analyzer, comprising:
    a particle concentrator adapted to collect and concentrate particles found within an aerosol;
    a sample collection surface adapted to accept particles provided by the particle concentrator;
    an energy source that provides energy that is adapted to induce fluorescence in the particles held by the sample collection surface;
    a detector adapted to detect the induced fluorescence; and
    a detection lens adapted to focus induced fluorescence on the detector.

12. A particle analyzer, comprising:
    a particle concentrator adapted to collect and concentrate particles found within an aerosol;
    a sample collection surface adapted to accept particles provided by the particle concentrator;
    an energy source that provides energy that is adapted to induce fluorescence in the particles held by the sample collection surface; and
    a detector adapted to detect the induced fluorescence, the detector comprising an array of pixels.

13. The particle analyzer of claim 12, wherein at least some of the pixels of the array of pixels are sensitive to a plurality of wavelengths, and are configured to provide a spatially resolved image.

14. The particle analyzer of claim 12, wherein at least some of the pixels of the array of pixels are sensitive to a single wavelength band.

15. A particle analyzer, comprising:
a particle concentrator adapted to collect and concentrate particles found within an aerosol;
a sample collection surface adapted to accept particles provided by the particle concentrator;

an energy source that provides energy that is adapted to induce fluorescence in the particles held by the sample collection surface; and a detector adapted to detect the induced fluorescence, wherein the detector includes a plurality of pixels sensitive to ultraviolet light and a plurality of pixels sensitive to visible light.

16. The particle analyzer of claim 15, wherein the plurality of pixels sensitive to ultraviolet light are arranged in a first linear array and the plurality of pixels sensitive to visible light are arranged in a second linear array.

17. The particle analyzer of claim 15, wherein at least some of the pixels sensitive to ultraviolet light and at least some of the pixels sensitive to visible light are positioned in an array in pair-wise fashion.

18. A particle analyzer, comprising:

a particle concentrator adapted to collect and concentrate particles found within an aerosol;

a sample collection surface adapted to accept particles provided by the particle concentrator;

an energy source that provides energy that is adapted to induce fluorescence in the particles held by the sample collection surface;

a detector adapted to detect the induced fluorescence; and a controller that is configured to control operation of the energy source and the detector;

wherein the controller is further configured to control a temperature modifying means that is thermally coupled to the sample collection surface in accordance with a programmed or programmable temperature profile.

19. A particle analyzer, comprising:

a particle concentrator adapted to collect and concentrate particles found within an aerosol;

a sample collection surface adapted to accept particles provided by the particle concentrator;

an energy source that provides energy that is adapted to induce fluorescence in the particles held by the sample collection surface;

a detector adapted to detect the induced fluorescence; and a humidity controller for controlling the humidity level around the sample collection surface.

20. A particle analyzer, comprising:

a particle concentrator adapted to collect and concentrate particles found within an aerosol;

a sample collection surface adapted to accept particles provided by the particle concentrator;

an energy source that provides energy that is adapted to induce fluorescence in the particles held by the sample collection surface;

a detector adapted to detect the induced fluorescence; and a pH controller for controlling the pH level at the sample collection surface.

21. The particle analyzer of claim 20, further comprising a chemical controller for selectively adding one or more chemicals to the sample collection surface.

22. The particle analyzer of claim 1, wherein the particle concentrator is adapted to provide mass sorted particles to the sample collection surface.

23. The particle analyzer of claim 1, wherein the energy source provides energy that induces at least some excitation fluorescence in a material of interest.

24. The particle analyzer of claim 1, further comprising a controller that is configured to control operation of the energy source and the detector.

25. The particle analyzer of claim 1 further comprising a chemical controller for selectively adding one or more chemicals to the sample collection surface.

26. A particle analyzer, comprising:

a particle concentrator adapted to collect and concentrate particles found within an aerosol;

a sample collection surface adapted to accept particles provided by the particle concentrator;

an energy source that provides energy that is adapted to induce fluorescence in the particles held by the sample collection surface; and a detector adapted to detect the induced fluorescence;

wherein the sample collection surface comprises an adsorbate.

27. A particle analyzer, comprising:

a particle concentrator adapted to collect and concentrate particles found within an aerosol;

a sample collection surface adapted to accept particles provided by the particle concentrator;

an energy source that provides energy that is adapted to induce fluorescence in the particles held by the sample collection surface; and a detector adapted to detect the induced fluorescence;

wherein the detector is adapted and configured to detect excitation fluorescence while being at least substantially blind to reflective energy from the energy source.

28. The particle analyzer of claim 27, wherein the detector is adapted and configured to detect excitation fluorescence while being positioned at an angle relative to the sample collection surface such that reflective energy from the energy source does not impinge upon the detector.

29. A particle analyzer, comprising:

a particle concentrator adapted to collect and concentrate particles found within an aerosol;

a sample collection surface adapted to accept particles provided by the particle concentrator;

an energy source that provides energy that is adapted to induce fluorescence in the particles held by the sample collection surface; and a detector adapted to detect the induced fluorescence;

wherein the detector is sensitive to a plurality of wavelengths.

30. A particle analyzer device, comprising:

a substrate;

a sample collection surface disposed over the substrate for collecting particles provided to the particle analyzer device; and temperature adjusting means thermally coupled to the sample collection surface for adjusting the temperature of the sample collection surface.

31. The particle analyzer device of claim 30, wherein the sample collection surface is at least partially thermally isolated from the substrate.

32. The particle analyzer device of claim 30, wherein the substrate includes a cavity, and the sample collection surface is at least partially suspended over the cavity.

33. The particle analyzer device of claim 32, further comprising a support member at least partially suspended over the cavity, where the sample collection surface is disposed on the support member.

34. The particle analyzer device of claim 33, wherein the support member comprises one or more legs connecting the support member to the substrate.

35. The particle analyzer device of claim 33, wherein the temperature adjusting means is disposed adjacent to or within the support member.

36. The particle analyzer device of claim 32, wherein the substrate comprises a silicon wafer.

37. The particle analyzer device of claim 30, wherein the temperature adjusting means comprises a resistive heater.

38. The particle analyzer device of claim 30, wherein the temperature adjusting means comprises a thermoelectric cooling element.

39. The particle analyzer device of claim 30, wherein the sample collection surface comprises an adsorbate.

40. The particle analyzer device of claim 30, wherein the sample collection surface comprises carbon nanotubes.

* * * * *